US012613217B2

(12) United States Patent
Miyakawa et al.

(10) Patent No.: US 12,613,217 B2
(45) Date of Patent: Apr. 28, 2026

(54) SEMICONDUCTOR DEVICE AND METHOD OF MANUFACTURING SEMICONDUCTOR DEVICE

(71) Applicant: Murata Manufacturing Co., Ltd., Nagaokakyo (JP)

(72) Inventors: Naruto Miyakawa, Nagaokakyo (JP); Shota Ushiba, Nagaokakyo (JP); Ayumi Shinagawa, Nagaokakyo (JP); Yuka Oka, Nagaokakyo (JP); Masahiko Kimura, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 679 days.

(21) Appl. No.: 17/886,527

(22) Filed: Aug. 12, 2022

(65) Prior Publication Data

US 2022/0390413 A1     Dec. 8, 2022

Related U.S. Application Data

(63) Continuation of application No. PCT/JP2020/040640, filed on Oct. 29, 2020.

(30) Foreign Application Priority Data

Mar. 9, 2020     (JP) ................................. 2020-040140

(51) Int. Cl.
*G01N 27/414* (2006.01)
*G01N 33/543* (2006.01)
(Continued)

(52) U.S. Cl.
CPC ..... *G01N 27/4146* (2013.01); *G01N 27/4148* (2013.01); *G01N 33/54373* (2013.01); *H10K 85/00* (2023.02); *H10K 10/40* (2023.02)

(58) Field of Classification Search
CPC ......... G01N 27/4148; G01N 33/54373; G01N 27/4145; G01N 27/4146; G01N 33/5438; H10D 30/67; H10K 10/40; H10K 85/00
See application file for complete search history.

(56) References Cited

U.S. PATENT DOCUMENTS 9,709,523 B1     7/2017   Osada et al.
2006/0065887 A1     3/2006   Tiano et al.
(Continued)

FOREIGN PATENT DOCUMENTS

JP      2005077237 A     3/2005
JP      2006156752 A     6/2006
(Continued)

OTHER PUBLICATIONS

Translation of Kazuhiro (JP 2007273874 A) (Year: 2006).*
(Continued)

*Primary Examiner* — William B Partridge
*Assistant Examiner* — Ilker Ozden
(74) *Attorney, Agent, or Firm* — Keating & Bennett, LLP

(57) ABSTRACT

A semiconductor device according to the present invention includes a substrate, a plurality of electrodes on the substrate, an insulator provided with one or a plurality of openings exposing at least one electrode among the plurality of electrodes on the substrate, the insulator covering at least a portion of the plurality of electrodes, and a semiconductor sheet on the insulator and one or a plurality of exposed portions exposed from the one or the plurality of openings on the substrate.

20 Claims, 24 Drawing Sheets

(51) Int. Cl.
    H10K 10/40        (2023.01)
    H10K 85/00        (2023.01)

(56)                References Cited

U.S. PATENT DOCUMENTS

| | | | |
|---|---|---|---|
| 2011/0227558 A1 | 9/2011 | Mannion et al. | |
| 2012/0132991 A1 | 5/2012 | Kuzumoto et al. | |
| 2016/0178568 A1* | 6/2016 | Cheng .................. | H01L 21/486 |
| | | | 257/253 |
| 2017/0067890 A1* | 3/2017 | Lin .................... | G01N 27/4148 |
| 2017/0181669 A1* | 6/2017 | Lin ........................ | G01N 33/66 |
| 2017/0350856 A1 | 12/2017 | Kobayashi et al. | |
| 2020/0141931 A1* | 5/2020 | Hoffman ............ | G01N 27/4146 |
| 2020/0244182 A1 | 7/2020 | Shimizu et al. | |
| 2021/0396748 A1* | 12/2021 | Ahn ........................ | G01N 27/12 |

FOREIGN PATENT DOCUMENTS

| | | | | | |
|---|---|---|---|---|---|
| JP | 2007273874 A | * | 10/2007 | | |
| JP | 2008505044 A | | 2/2008 | | |
| JP | 2010151659 A | | 7/2010 | | |
| JP | 2016065746 A | | 4/2016 | | |
| JP | 2017166947 A | | 9/2017 | | |
| WO | 2011065083 A1 | | 6/2011 | | |
| WO | WO-2015007369 A1 | * | 1/2015 | ......... | G01N 27/4145 |
| WO | 2016021693 A1 | | 2/2016 | | |
| WO | 2019063493 A1 | | 4/2019 | | |
| WO | 2019087937 A1 | | 5/2019 | | |

OTHER PUBLICATIONS

Han, E., Yu, J., Annevelink, E. et al. Ultrasoft slip-mediated bending in few-layer graphene. Nat. Mater. 19, 305â309 (2020). https://doi.org/10.1038/s41563-019-0529-7 (Year: 2019).*

Liu et al., van der Waals Contact Engineering of Graphene Field-Effect Transistors for Large-Area Flexible Electronics, ACS Nano 2019 13 (3), 3257-3268, DOI: 10.1021/acsnano.8b09019 (Year: 2019).*

Translation of JP 2007273874 A (Year: 2007).*

International Search Report in PCT/JP2020/040640, mailed Jan. 12, 2021, 4 pages.

Written Opinion in PCT/JP2020/040640, mailed Jan. 12, 2021, 3 pages.

Office Action in JP2022-505753, mailed Jul. 11, 2023, 3 pages.

* cited by examiner

FIG. 6

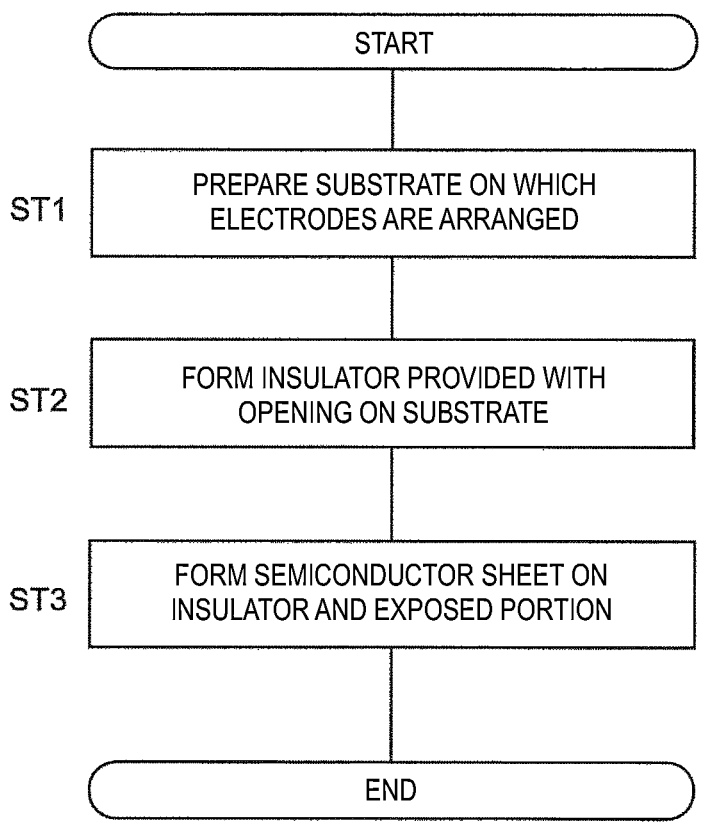

```
            ┌─────────────────────────────┐
            │           START             │
            └─────────────────────────────┘
                          │
            ┌─────────────────────────────┐
     ST1    │  PREPARE SUBSTRATE ON WHICH  │
            │   ELECTRODES ARE ARRANGED    │
            └─────────────────────────────┘
                          │
            ┌─────────────────────────────┐
     ST2    │  FORM INSULATOR PROVIDED WITH │
            │    OPENING ON SUBSTRATE      │
            └─────────────────────────────┘
                          │
            ┌─────────────────────────────┐
     ST3    │  FORM SEMICONDUCTOR SHEET ON  │
            │ INSULATOR AND EXPOSED PORTION │
            └─────────────────────────────┘
                          │
            ┌─────────────────────────────┐
            │            END              │
            └─────────────────────────────┘
```

FIG. 7A

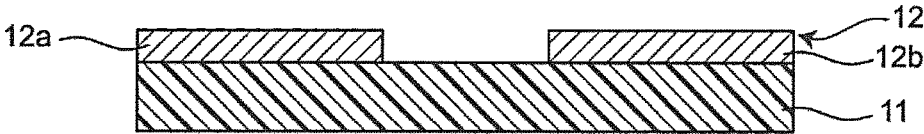

SEMICONDUCTOR DEVICE AND METHOD OF MANUFACTURING SEMICONDUCTOR DEVICE

CROSS REFERENCE TO RELATED APPLICATIONS

This application claims the benefit of priority to Japanese Patent Application No. 2020-040140 filed on Mar. 9, 2020 and is a Continuation application of PCT Application No. PCT/JP2020/040640 filed on Oct. 29, 2020. The entire contents of each application are hereby incorporated herein by reference.

BACKGROUND OF THE INVENTION

1. Field of the Invention

The present invention relates to a semiconductor device and a method of manufacturing a semiconductor device.

2. Description of the Related Art

For example, as a semiconductor device, International Publication No. 2016/021693 discloses a field effect transistor and a sensor using the same. In the field effect transistor described in International Publication No. 2016/021693, particles constituted by a non-metallic material are used as growth nuclei, and a channel of the field effect transistor is constituted by a single wall carbon nanotube thin film grown by a chemical vapor deposition method.

In recent years, there has been a demand for improving the performance of semiconductor devices.

SUMMARY OF THE INVENTION

Preferred embodiments of the present invention provide semiconductor devices that are each able to improve the device performance, and methods of manufacturing such semiconductor devices.

A semiconductor device according to a preferred embodiment of the present invention includes a substrate, a plurality of electrodes on the substrate, an insulator including one or a plurality of openings exposing at least one electrode among the plurality of electrodes on the substrate, the insulator covering at least a portion of the plurality of electrodes, and a semiconductor sheet on the insulator and one or a plurality of exposed portions exposed from the one or the plurality of openings on the substrate.

A method of manufacturing a semiconductor device according to a preferred embodiment of the present invention includes preparing a substrate on which a plurality of electrodes are provided, forming an insulator provided with one or a plurality of openings exposing at least one electrode among the plurality of electrodes on the substrate, the insulator covering at least a portion of the plurality of electrodes, and forming a semiconductor sheet on the insulator and one or a plurality of exposed portions exposed from the one or the plurality of openings on the substrate.

According to preferred embodiments of the present invention, it is possible to provide semiconductor devices that are each able to improve performance and methods of manufacturing such semiconductor devices.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 6 is a flowchart of an example of a method of manufacturing a semiconductor device according to Preferred Embodiment 1 of the present invention.

FIG. 7A is a schematic view illustrating an example of a process of the method of manufacturing the semiconductor device according to Preferred Embodiment 1 of the present invention.

DETAILED DESCRIPTION OF THE PREFERRED EMBODIMENTS

Figure 1:
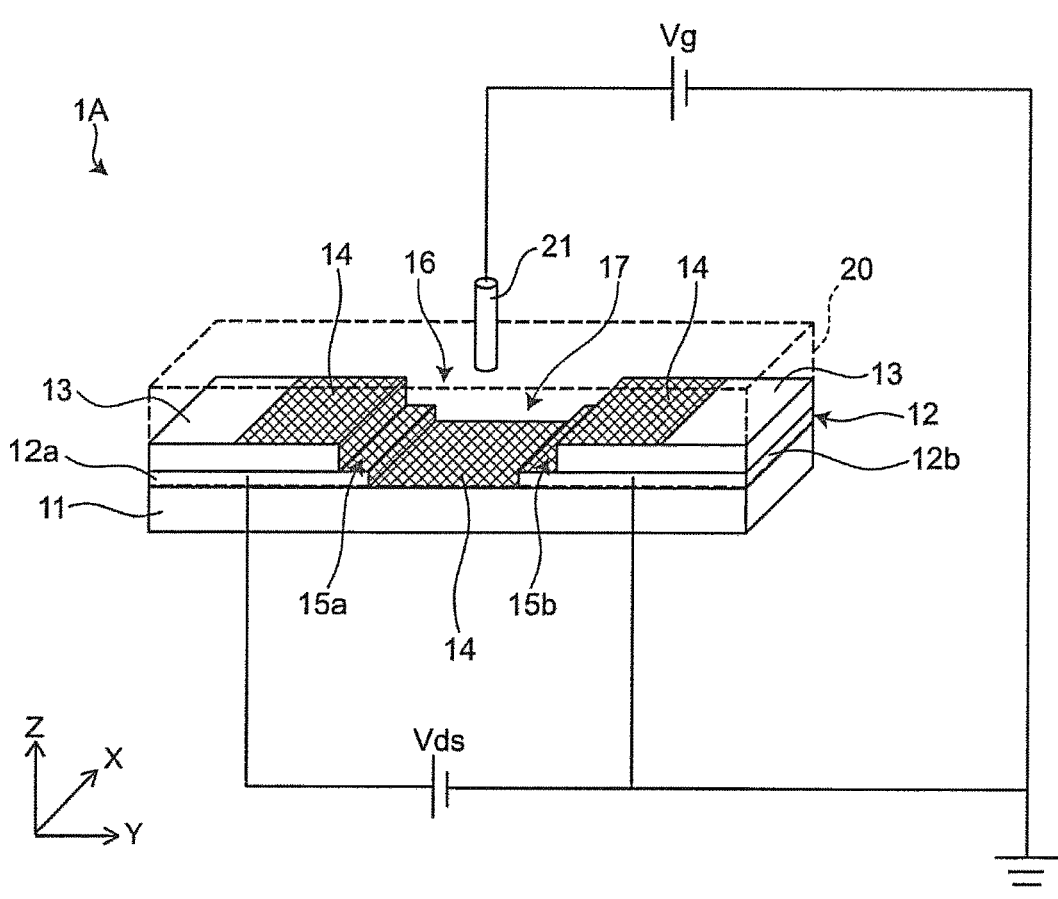
FIG. 1 is a schematic perspective view illustrating an example of a main configuration of a semiconductor device according to Preferred Embodiment 1 of the present invention.

In a method of manufacturing a semiconductor device, such as a field effect transistor, electrode wiring is performed on a plurality of semiconductor sheets on a substrate, and then, coating is performed with an insulator. Then, the insulator on the semiconductor sheet is removed by photolithography or the like to make a semiconductor channel.

Further, there is a method of forming a semiconductor channel using a resist. In this method, a resist film is formed at a position where a semiconductor channel is to be provided on a substrate, and the resist film is coated with an insulator. The semiconductor channel is formed by removing the resist film after coating with the insulator.

However, it is difficult for the method of manufacturing described above to improve the performance of a semiconductor device. When the insulator on a semiconductor sheet is removed by, for example, photolithography or the like, the insulator may remain on a surface of the semiconductor sheet. Also, when a resist is used, the resist may remain on the surface of the semiconductor sheet. As described above, the surface of the semiconductor sheet may be contaminated by the insulator and the resist, and the electrical characteristics of the semiconductor sheet are deteriorated.

When the semiconductor device is used as a biosensor to detect viruses, a plurality of receptors to capture target molecules are provided on the semiconductor sheet. In this case, no receptor can be placed in a portion where the insulator or the resist remains on the surface of the semiconductor sheet. Thus, the target molecule cannot be captured in the portion where the receptor is not placed on the semiconductor sheet. Thus, it is difficult to improve the accuracy of virus detection.

The inventors of preferred embodiments of the present invention discovered a method of manufacturing a semiconductor device by coating a plurality of electrodes on a substrate with an insulator and then transferring a semiconductor sheet from above the insulator, and have led to the following invention.

A semiconductor device according to a preferred embodiment of the present invention preferably includes a substrate, a plurality of electrodes on the substrate, an insulator including one or a plurality of openings exposing at least one electrode among the plurality of electrodes on the substrate, the insulator covering at least a portion of the plurality of electrodes, and a semiconductor sheet on the insulator and one or a plurality of exposed portions exposed from the one or the plurality of openings on the substrate. With this configuration, the performance of the device can be improved.

In the semiconductor device, the plurality of electrodes may include a first electrode, and a second electrode located at an interval from the first electrode, at least one of a portion of the first electrode and a portion of the second electrode may be positioned at the one or the plurality of exposed portions, and the semiconductor sheet may be connected to the first electrode and the second electrode. With this configuration, the performance of the device can be further improved.

A region including an end portion of the first electrode opposing the second electrode and a region including an end portion of the second electrode opposing the first electrode may be positioned at the exposed portion. With this configuration, the performance of the device can be further improved.

In the semiconductor device, the insulator may include a coupling insulating portion positioned across the first electrode and the second electrode, the plurality of openings may include a first opening exposing a portion of the first electrode on the substrate and a second opening exposing a portion of the second electrode on the substrate. The plurality of exposed portions may include a first exposed portion exposed from the first opening and a second exposed portion exposed from the second opening on the substrate, and the semiconductor sheet may be provided continuously on the coupling insulating portion, the first exposed portion, and the second exposed portion. With this configuration, the performance of the device can be further improved.

In the plurality of exposed portions, a gap may be provided among a side wall of the insulator provided with the plurality of openings, the semiconductor sheet, and the substrate. With such a configuration, stress applied to the semiconductor sheet can be relaxed, and the performance of the device can be further improved.

The semiconductor sheet may include a first semiconductor sheet on the insulator, and a second semiconductor sheet separated from the first semiconductor sheet and on the exposed portion. With such a configuration, electrical short circuiting of the semiconductor sheet can be prevented.

In the semiconductor device, an end portion of the second semiconductor sheet may be bent in a thickness direction of the second semiconductor sheet. With such a configuration, the second semiconductor sheet can be easily checked.

In the semiconductor device, the semiconductor sheet may be made from any one of graphene, a carbon nanotube, an organic semiconductor, MXENES, and a transition metal dichalcogenide layered material. With this configuration, the performance of the device can be further improved.

The semiconductor device may further include a plurality of receptors on the semiconductor sheet and configured to capture a target molecule. With such a configuration, the target molecule can be captured.

The semiconductor device may further include a calculator configured to receive an electric signal output from the semiconductor sheet and configured to calculate an amount of the target molecule based on the electric signal. With such a configuration, the amount of the target molecule can be calculated.

In the semiconductor device, the semiconductor sheet may be in close contact with the insulator and the one or the plurality of exposed portions by van der Waals force. With such a configuration, the semiconductor sheet can be easily fixed.

A method of manufacturing a semiconductor device according to a preferred embodiment of the present invention includes preparing a substrate on which a plurality of electrodes are provided, forming an insulator provided with one or a plurality of openings exposing at least one electrode among the plurality of electrodes on the substrate, the insulator covering at least a portion of the plurality of electrodes, and forming a semiconductor sheet on the insulator and one or a plurality of exposed portions exposed from the one or the plurality of openings on the substrate. With such a configuration, it is possible to manufacture a semiconductor device with improved device performance.

In the method of manufacturing, the plurality of electrodes may include a first electrode and a second electrode at an interval from the first electrode, and at least one of a portion of the first electrode and a portion of the second electrode may be positioned at the one or the plurality of exposed portions, and the semiconductor sheet may electrically connect the first electrode and the second electrode to each other. With such a configuration, it is possible to manufacture a semiconductor device with further improved device performance.

In the method of manufacturing, a region including an end portion of the first electrode opposing the second electrode and a region including an end portion of the second electrode opposing the first electrode may be positioned at the exposed portion. With such a configuration, it is possible to manufacture a semiconductor device with further improved device performance.

In the method of manufacturing, the forming of the insulator may include forming a coupling insulating portion across the first electrode and the second electrode, and forming, in the insulator, a first opening exposing a portion of the first electrode on the substrate and a second opening exposing a portion of the second electrode on the substrate, and the forming of the semiconductor sheet may include continuously forming the semiconductor sheet on the coupling insulating portion, a first exposed portion exposing a portion of the first electrode from the first opening, and a second exposed portion exposing a portion of the second electrode from the second opening. With such a configuration, it is possible to manufacture a semiconductor device with further improved device performance.

In the method of manufacturing, the forming of the insulator may include forming, in the insulator, an opening exposing a portion of the first electrode and a portion of the second electrode on the substrate, and the forming of the semiconductor sheet may include separating the semiconductor sheet into a first semiconductor sheet on the insulator and a second semiconductor sheet on an exposed portion exposed from the opening on the substrate. With such a configuration, an electrical short circuiting of the semiconductor sheet can be prevented, and a semiconductor device with further improved performance can be manufactured.

In the method of manufacturing, the separating may include cutting the semiconductor sheet by a step formed between the insulator and the substrate at the opening. With such a configuration, the semiconductor sheet can be easily separated.

Hereinafter, Preferred Embodiment 1 of the present invention will be described with reference to the accompanying drawings. Additionally, in each of the drawings, elements are illustrated in an exaggerated manner for ease of explanation.

Preferred Embodiment 1

Figure 2:
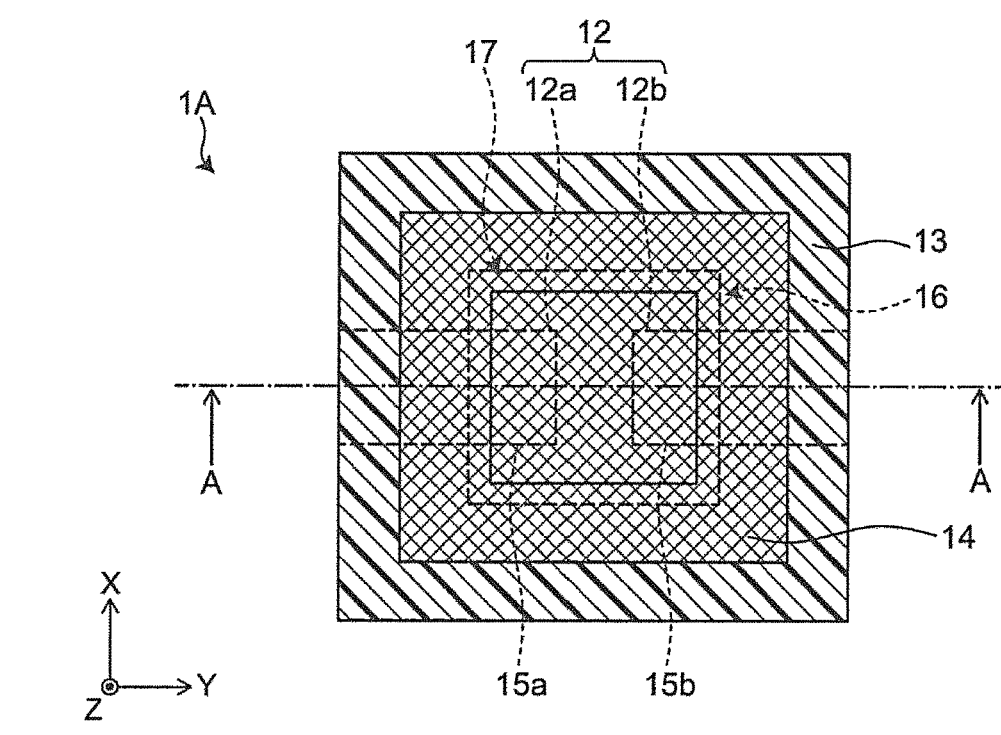
FIG. 2 is a schematic plan view illustrating an example of a main configuration of the semiconductor device according to Preferred Embodiment 1 of the present invention.
Figure 3:
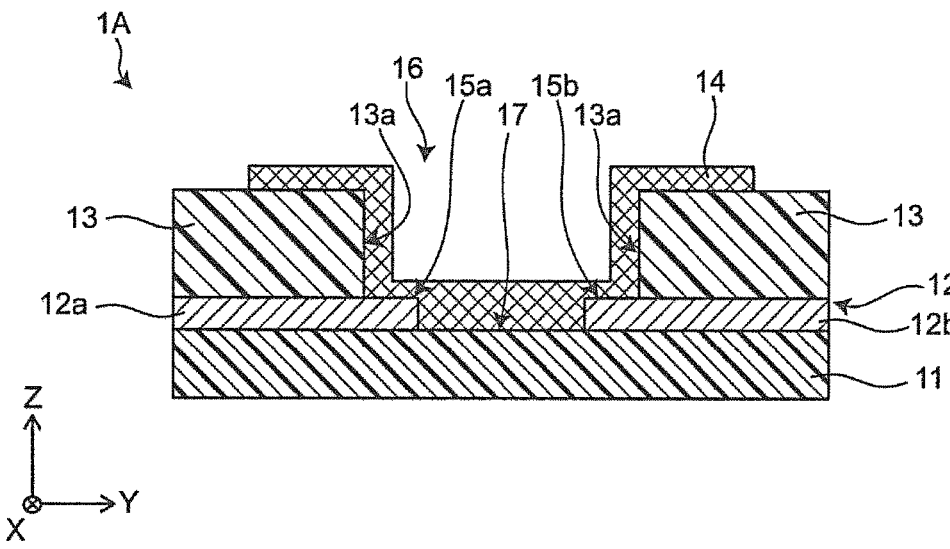
FIG. 3 is a schematic cross-sectional view of the semiconductor device in FIG. 2 taken along a line A-A.

FIG. 1 is a schematic perspective view illustrating an example of a main configuration of a semiconductor device 1A according to Preferred Embodiment 1 of the present invention. FIG. 2 is a schematic plan view illustrating an example of a main configuration of the semiconductor device 1A according to Preferred Embodiment 1 of the present invention. FIG. 3 is a schematic cross-sectional view of the semiconductor device 1A in FIG. 2 taken along a line A-A. In FIG. 2 and FIG. 3, an electrolyte solution 20 and a third electrode 21 are not illustrated. X, Y, and Z directions in the figures indicate a depth direction, a width direction and a height direction of the semiconductor device 1A, respectively.

As illustrated in FIGS. 1 to 3, the semiconductor device 1A includes a substrate 11, a plurality of electrodes 12, an insulator 13, and a semiconductor sheet 14.

In Preferred Embodiment 1, a field effect transistor will be described as an example of the semiconductor device 1A. In the semiconductor device 1A, the plurality of electrodes 12 include a first electrode 12a and a second electrode 12b that are on the substrate 11. The first electrode 12a is preferably a drain electrode, and the second electrode 12b is preferably a source electrode. A drain-source voltage Vds is applied between the first electrode 12a and the second electrode 12b. The semiconductor sheet 14 is in the electrolyte solution 20. The third electrode 21 is in the electrolyte solution 20. The third electrode 21 is a gate electrode to which a gate voltage Vg is applied.

Hereinafter, a detailed configuration of the semiconductor device 1A will be described.

The substrate 11 is made of an insulator material. For example, the substrate 11 is preferably made of an insulator material such as $SiO_2$. The substrate 11 has a plate shape. A wiring pattern including a plurality of electrodes 12 is provided on the substrate 11.

The plurality of electrodes 12 are on the substrate 11. The plurality of electrodes 12 are spaced apart at intervals. To be specific, the plurality of electrodes 12 include the first electrode 12a on the substrate 11 and the second electrode 12b spaced at an interval from the first electrode 12a. Further, the first electrode 12a and the second electrode 12b are on the substrate 11 to oppose each other.

The plurality of electrodes 12 have a plate shape. The plurality of electrodes 12 are made of a conductive material. For example, the plurality of electrodes 12 are preferably made of a conductive material such as Cu, Ti, Ni, Cr, Au, Pt or the like.

The insulator 13 covers at least a portion of the plurality of electrodes 12 on the substrate 11. For example, the insulator 13 is preferably made of an insulator material such as ceramics such as $SiO_2$, $Si_3N_4$, $Al_2O_3$, $HfO_2$ and the like, resin materials such as epoxy resin, polyimide resin, silicone resin, fluororesin, photoresists and the like, or two dimensional insulator materials such as boron nitride, or the like.

In Preferred Embodiment 1, since the pattern is formed by photolithography, the material for forming the insulator 13 is preferably a photosensitive material, for example.

The insulator 13 is provided to cover a portion of the first electrode 12a and a portion of the second electrode 12b and to expose a portion of the substrate 11, a portion of the first electrode 12a, and a portion of the second electrode 12b. The insulator 13 includes an opening 16 exposing at least one electrode among the plurality of electrodes 12 on the substrate 11.

As illustrated in FIG. 2, the opening 16 has a rectangular or substantially rectangular shape when the semiconductor device 1A is viewed from the height direction (Z direction). The opening 16 exposes a portion of the substrate 11. This defines an exposed portion 17 exposed from the opening 16 on the substrate 11.

In Preferred Embodiment 1, a region 15a including an end portion of the first electrode 12a opposing the second electrode 12b and a region 15b including an end portion of the second electrode 12b opposing the first electrode 12a are positioned at the exposed portion 17.

The semiconductor sheet 14 is made of a semiconductor. The semiconductor sheet 14 is preferably made of, for example, a conductive material and is a sheet that converts adhesion of molecules into an electric signal (for example, a current signal) and outputs the electric signal. When molecules adhere to the semiconductor sheet 14, the electrical characteristics (for example, current-voltage characteristics) change. For example, the semiconductor sheet 14 is made of any one of graphene, carbon nanotubes, organic semiconductors, MXENES, and transition metal dichalcogenide layered materials. In Preferred Embodiment 1, the semiconductor sheet 14 is preferably made of graphene. Graphene has higher carrier mobility than those of other semiconductor materials. As a result, the amount of a current modulated by the same adhered molecule can be made larger than those of other semiconductor materials.

The semiconductor sheet 14 is preferably, for example, equal to or larger than about 0.3 nm and equal to or less than about 300 nm. The semiconductor sheet 14 is on the insulator 13 and the exposed portion 17 exposed from the opening 16 on the substrate 11. Specifically, the semiconductor sheet 14 is on an upper surface of the insulator 13. The upper surface of the insulator 13 is a surface opposite to a surface being in contact with the substrate 11 and the plurality of electrodes 12 in the height direction (Z direction) of the semiconductor device 1A. In addition, the semiconductor sheet 14 covers the region 15a including the end portion of the first electrode 12a opposing the second electrode 12b and the region 15b including the end portion of the second electrode 12b opposing the first electrode 12a that are positioned at the exposed portion 17.

In Preferred Embodiment 1, the semiconductor sheet 14 is preferably continuously provided on the insulator 13 and the exposed portion 17. To be specific, the semiconductor sheet 14 is continuously provided on the upper surface of the insulator 13, a side wall 13a of the insulator, and the exposed portion 17. Here, "continuously provided" means that all portions of the semiconductor sheet 14 are in a state of being connected. In other words, one semiconductor sheet 14 covers the insulator 13 and the exposed portion 17.

The semiconductor sheet 14 is in close contact with the insulator 13 and the exposed portion 17 by van der Waals force. The semiconductor sheet 14 is connected to a portion of the first electrode 12a and a portion of the second electrode 12b in the exposed portion 17. That is, the semiconductor sheet 14 is electrically connected to the first electrode 12*a* and the second electrode 12*b*. In this way, the semiconductor sheet 14 can be used as a semiconductor channel. For example, polymethyl methacrylate (PMMA) may be provided as a protection film on the surface of the semiconductor sheet 14.

Figure 4:
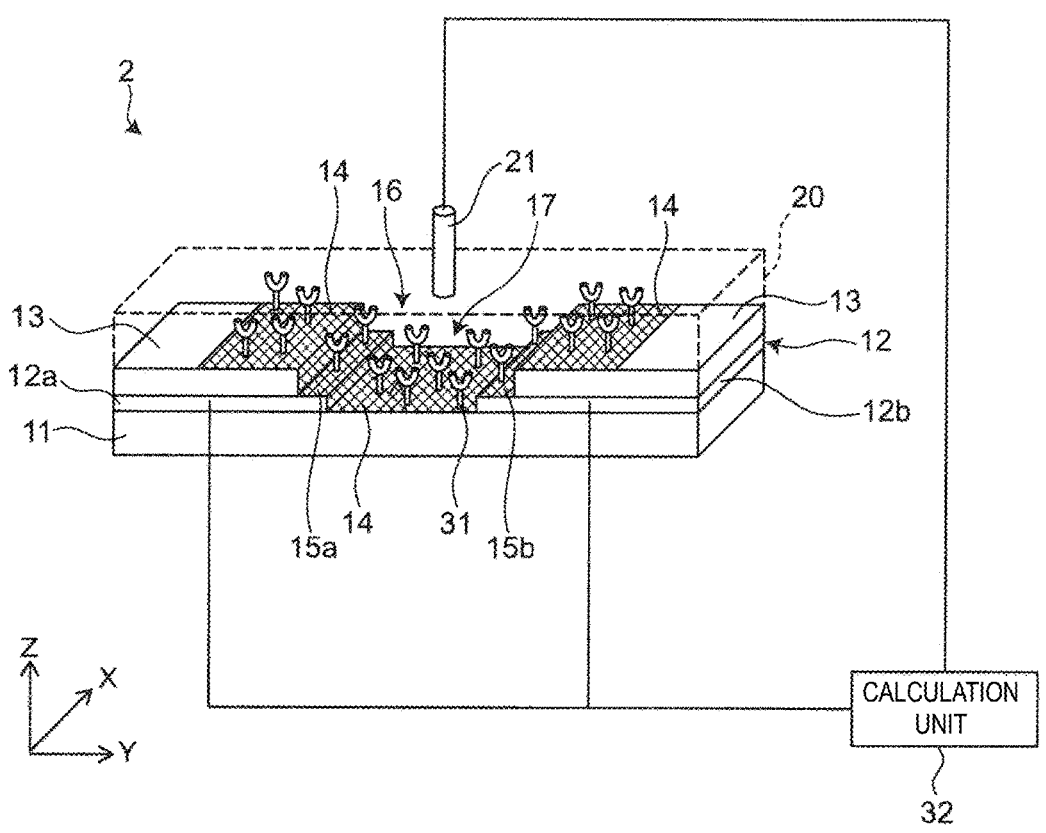
FIG. 4 is a schematic perspective view of an example of a sensor according to Preferred Embodiment 1 of the present invention.
Figure 5:
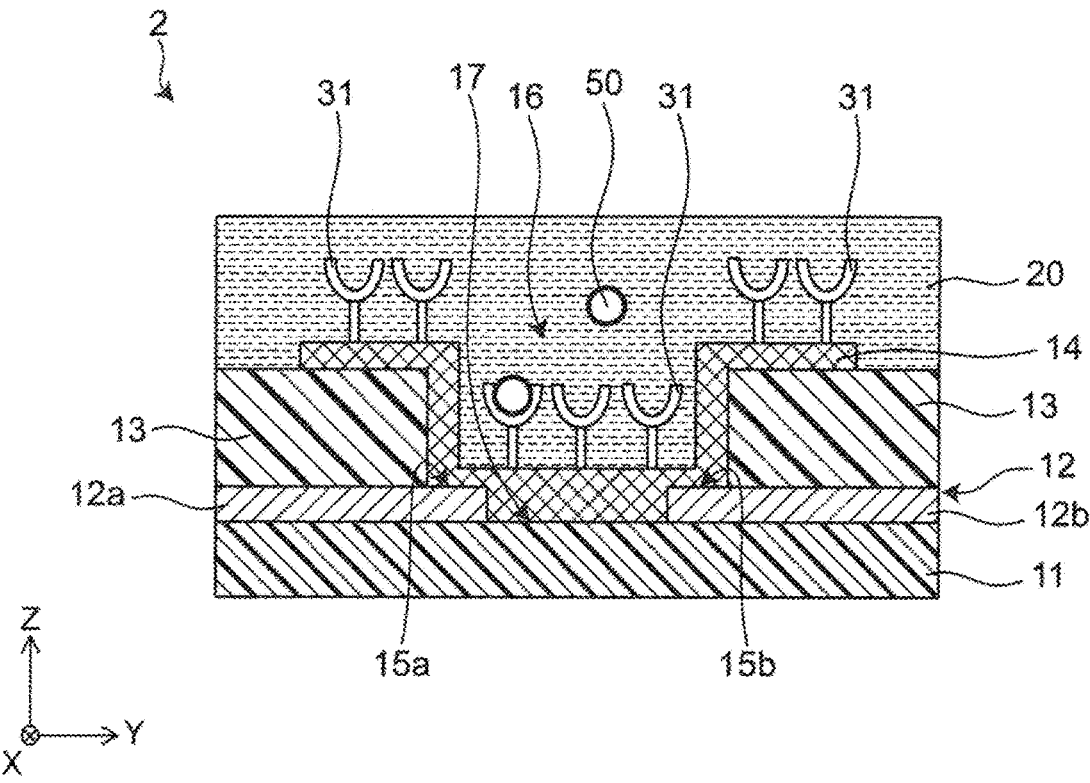
FIG. 5 is a schematic cross-sectional view of the sensor in FIG. 4.

Next, an example in which the semiconductor device 1A is used as a sensor will be described with reference to FIG. 4 and FIG. 5. FIG. 4 is a schematic perspective view of an example of a sensor 2 according to Preferred Embodiment 1 of the present invention. FIG. 5 is a schematic cross-sectional view of the sensor 2 in FIG. 4. The sensor 2 illustrated in FIG. 4 and FIG. 5 is a biosensor to detect a target molecule 50 such as a virus. As illustrated in FIG. 4 and FIG. 5, the sensor 2 includes a plurality of receptors 31 and a calculator 32. The other configurations of the sensor 2 are the same as or similar to those of the semiconductor device 1A.

The plurality of receptors 31 are on the semiconductor sheet 14 and capture the target molecules 50. The plurality of receptors 31 are on the semiconductor sheet 14 which is on the insulator 13 and the exposed portion 17. The plurality of receptors 31 are in the electrolyte solution 20.

The plurality of receptors 31 capture the target molecules 50 such as, for example, viruses that are detection targets. The plurality of receptors 31 capture the target molecules 50 present in the electrolyte solution 20.

The calculator 32 receives the electric signal output from the semiconductor sheet 14 and calculates the amount of the target molecules 50 based on the electric signal. The calculator 32 quantitatively detects the target molecules 50 based on the electric signal.

The calculator 32 is connected to the first electrode 12*a*, the second electrode 12*b*, and the third electrode 21. Here, the first electrode 12*a* is a drain electrode and the second electrode 12*b* is a source electrode. The calculator 32 controls the drain-source voltage Vds applied between the first electrode 12*a* and the second electrode 12*b* and the gate voltage Vg applied to the third electrode 21.

When the target molecules 50 are captured by the receptors 31, the electrical characteristics (for example, a current-voltage characteristic) of the semiconductor sheet 14 change according to surface charges of the target molecules 50. Due to the change in the electrical characteristics of the semiconductor sheet 14, the electric signal (for example, a current signal) output from the semiconductor sheet 14 also changes.

The calculator 32 receives the electric signal output from the semiconductor sheet 14 and calculates the amount of the target molecules 50 based on the electric signal. It is known that there is a correlation between the amount of the target molecules 50 and the amount of change in the electric signal. The calculator 32 calculates the amount of the target molecules 50 based on the amount of change in the electric signal. Thus, the presence or absence of the target molecule 50 can be determined and/or a concentration thereof can be calculated.

The calculator 32 can be configured by using a semiconductor element or the like. The calculator 32 can be provided by, for example, a microcomputer, a CPU, an MPU, a GPU, a DSP, an FPGA, an ASIC, a discrete semiconductor, or an LSI. The function of the calculator 32 may be configured only by using hardware, or may be implemented by a combination of hardware and software. The calculator 32 achieves a predetermined function by reading data and programs stored in a storage (not illustrated) in the calculator 32 and performing various types of calculation processing. The storage can be configured by, for example, a hard disk drive (HDD), an SSD, a RAM, a DRAM, a ferroelectric memory, a flash memory, a magnetic disk, or a combination thereof.

Method of Manufacturing

An example of a method of manufacturing the semiconductor device 1A will be described. FIG. 6 is a flowchart of an example of a method of manufacturing the semiconductor device 1A according to Preferred Embodiment 1 of the present invention. FIGS. 7A to 7E are schematic views illustrating an example of processes of the method of manufacturing the semiconductor device 1A according to Preferred Embodiment 1 of the present invention. Steps that will be described below are executed by a manufacturing apparatus.

As illustrated in FIG. 6, in a step ST1, the substrate 11 on which a plurality of electrodes 12 are provided is prepared. To be specific, as illustrated in FIG. 7A, in the step ST1, the substrate 11 on which the first electrode 12*a* and the second electrode 12*b* are provided is prepared. For example, the step ST1 is performed by a metal film forming apparatus represented by a sputtering apparatus or an electron beam (EB) vapor deposition apparatus included in the manufacturing apparatus.

Figure 8:
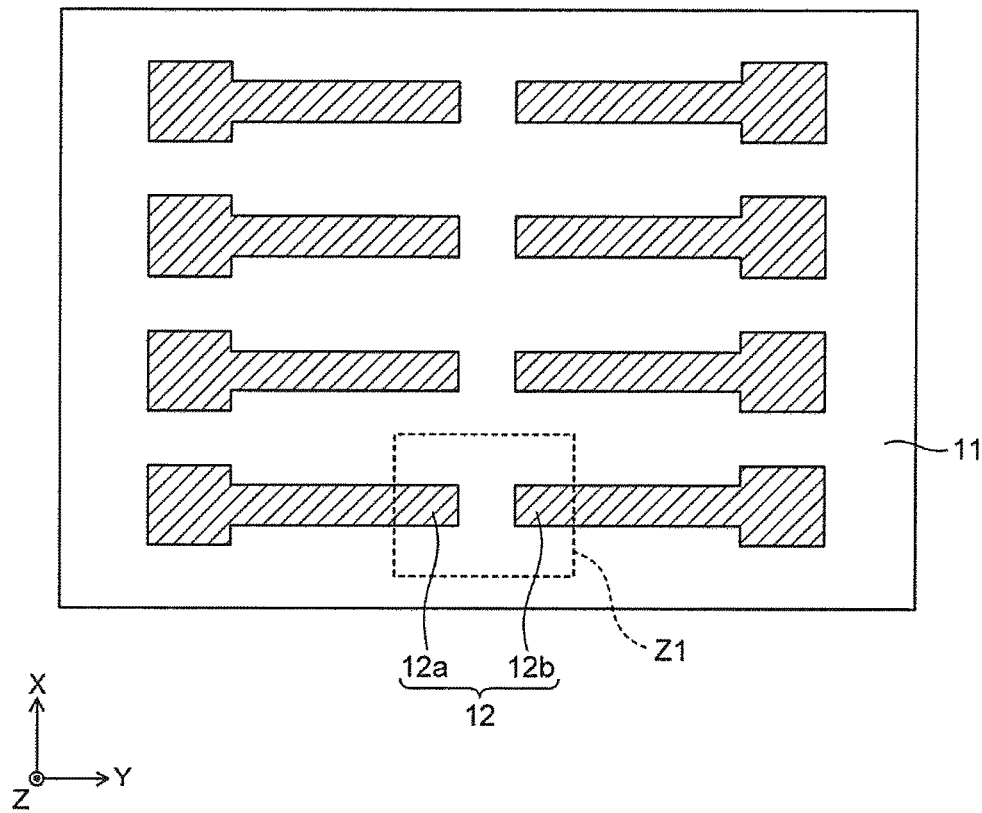
FIG. 8 is a schematic plan view illustrating an example of a substrate including a plurality of electrodes.
Figure 9:
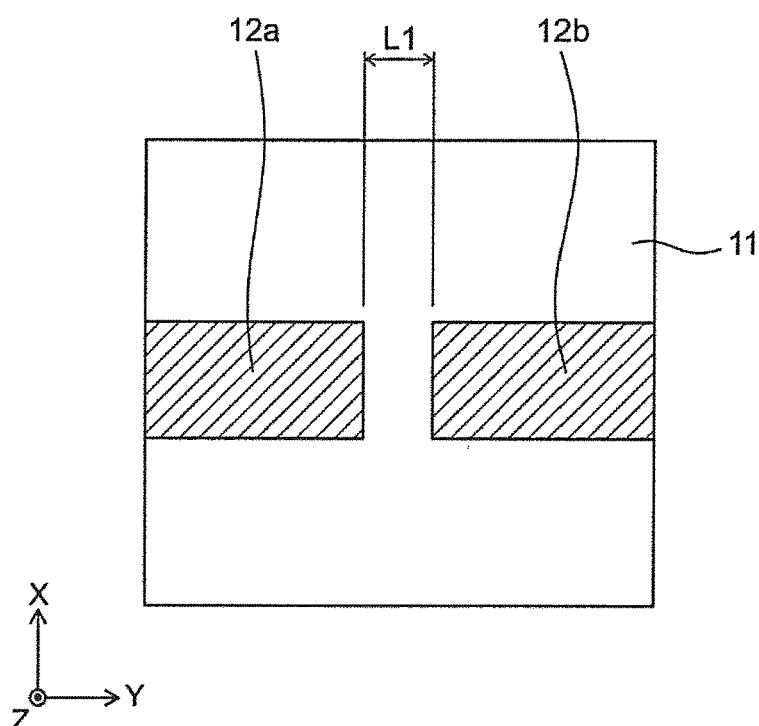
FIG. 9 is a schematic enlarged view of a portion of the substrate in FIG. 8.

FIG. 8 is a schematic plan view illustrating an example of the substrate 11 on which the plurality of electrodes 12 are provided. FIG. 9 is a schematic enlarged view in which a portion of the substrate 11 in FIG. 8 is enlarged. FIG. 9 is an enlarged schematic view of a Z1 portion in FIG. 8. As illustrated in FIG. 8 and FIG. 9, a wiring pattern including the plurality of electrodes 12 is provided on the substrate 11. For example, the wiring pattern can be formed on the substrate 11 by photolithography.

In the plurality of electrodes 12, the first electrode 12*a* and the second electrode 12*b* are provided at a predetermined interval L1. For example, the predetermined interval L1 is larger than or equal to about 50 nm and less than or equal to about 5 mm. Thus, when the substrate 11 is viewed from the height direction (Z direction), the substrate 11 is interposed between the first electrode 12*a* and the second electrode 12*b*.

In Preferred Embodiment 1, electrode patterns including the first electrode 12*a* and the second electrode 12*b* arranged at the predetermined interval L1 are defined as one set. A wiring pattern that is provided on the substrate 11 and that is illustrated in FIG. 8 includes a plurality of sets.

Returning to FIG. 6, in a step ST2, the insulator 13 is formed on the substrate 11. To be specific, in the step ST2, the insulator 13 provided with the opening 16 exposing a portion of the plurality of electrodes 12 is formed on the substrate 11. The insulator 13 exposes a portion of the plurality of electrodes 12 from the opening 16 and covers a portion of the plurality of electrodes 12. In Preferred Embodiment 1, the insulator 13 covers a portion of the first electrode 12*a* and a portion of the second electrode 12*b*, and exposes a portion of the substrate 11, a portion of the first electrode 12*a*, and a portion of the second electrode 12*b*. For example, the step ST2 is performed by an insulating film forming apparatus represented by a spin coater, various vapor deposition apparatuses, and a CVD apparatus, and a photolithography apparatus that are included in the manufacturing apparatus.

Figure 7B:
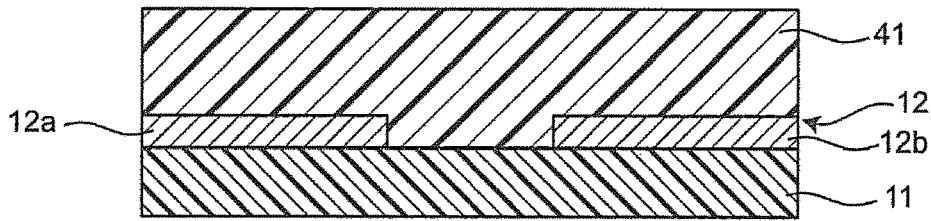
FIG. 7B is a schematic view illustrating an example of a process of the method of manufacturing the semiconductor device according to Preferred Embodiment 1 of the present invention.
Figure 7C:
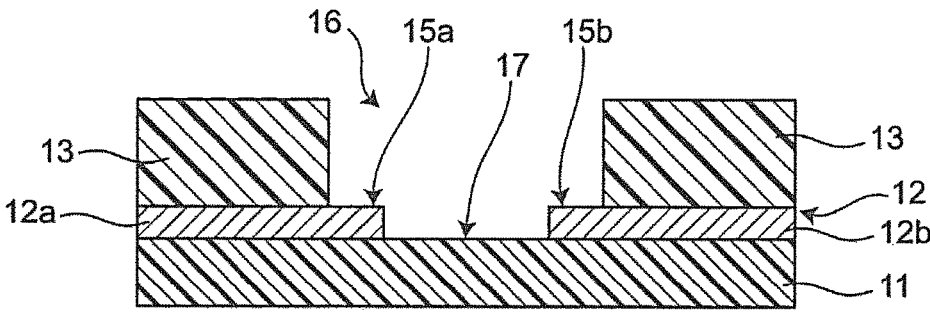
FIG. 7C is a schematic view illustrating an example of a process of the method of manufacturing the semiconductor device according to Preferred Embodiment 1 of the present invention.

As illustrated in FIG. 7B, an insulating coating material 41 is preferably film-formed on the substrate 11 on which the plurality of electrodes 12 are provided. For example, the insulating coating material 41 is applied onto the substrate 11 and cured. As illustrated in FIG. 7C, a portion of the insulating coating material 41 is removed by photolithography. Thus, the insulator 13 provided with the opening 16 is formed on the substrate 11.

Figure 10:
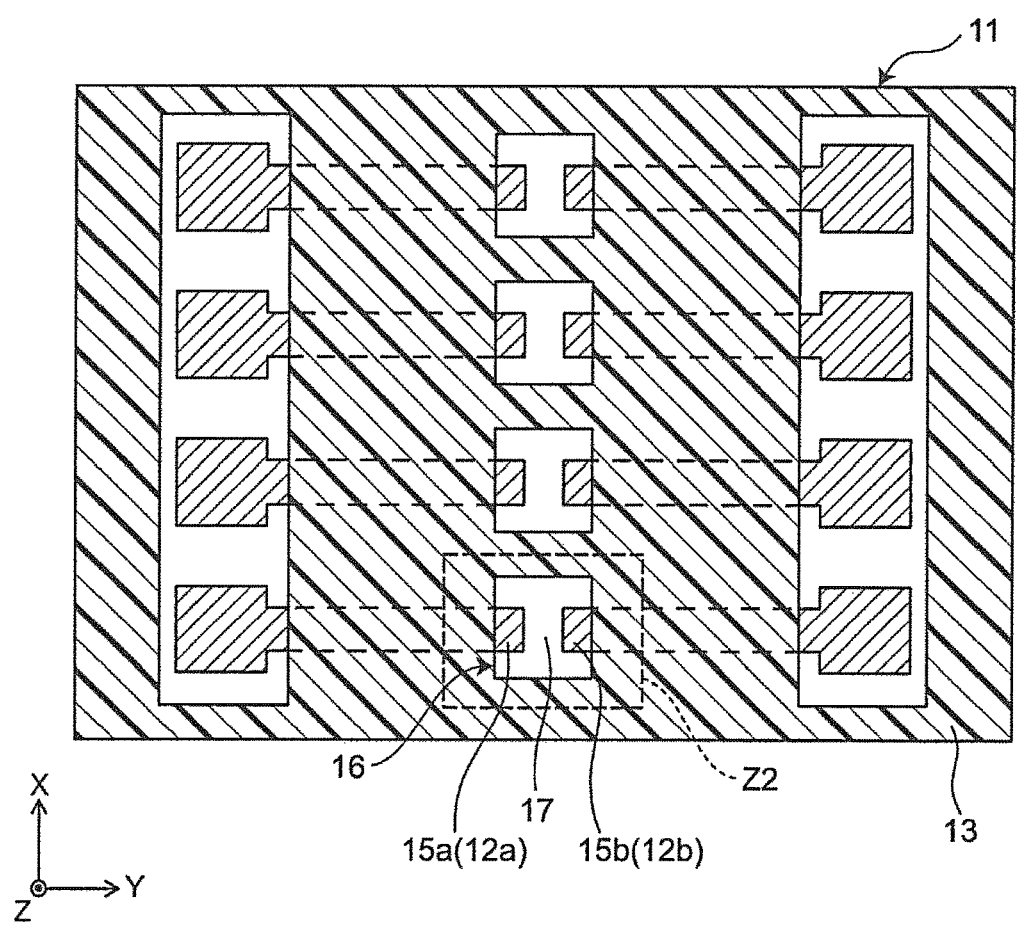
FIG. 10 is a schematic plan view illustrating an example of the substrate with an insulator.
Figure 11:
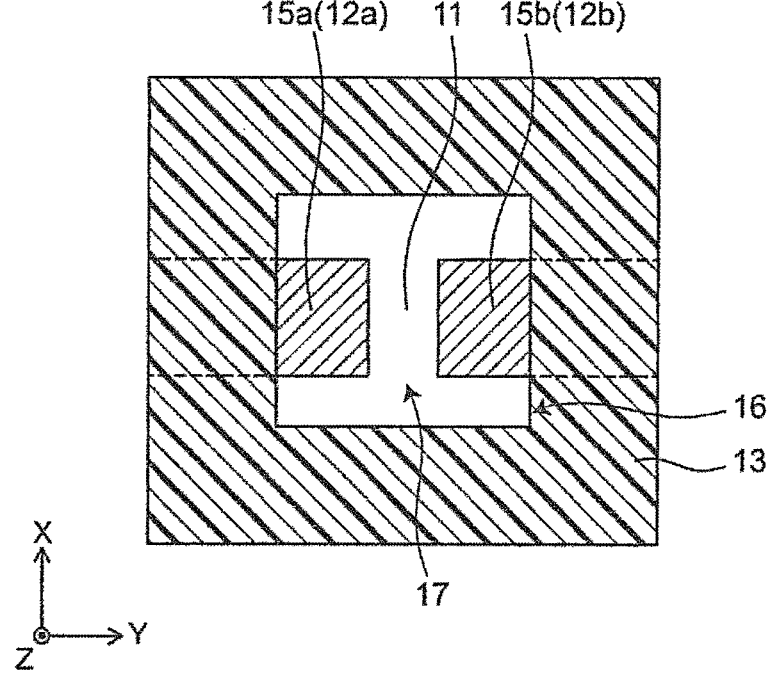
FIG. 11 is a schematic enlarged view of an exposed portion of the substrate in FIG. 10.

FIG. 10 is a schematic plan view illustrating an example of the substrate 11 on which the insulator 13 is disposed. FIG. 11 is a schematic enlarged view of the exposed portion 17 of the substrate 11 in FIG. 10. FIG. 11 is an enlarged schematic view of a Z2 portion in FIG. 10. As illustrated in FIG. 10 and FIG. 11, when the substrate 11 is viewed from the height direction (Z direction), a portion of the first electrode 12a and a portion of the second electrode 12b are positioned at the exposed portion 17 exposed from the opening 16 on the substrate 11. In Preferred Embodiment 1, the region 15a including an end portion of the first electrode 12a opposing the second electrode 12b and the region 15b including an end portion of the second electrode 12b opposing the first electrode 12a are positioned at the exposed portion 17.

Returning to FIG. 6, in a step ST3, the semiconductor sheet 14 is formed on the insulator 13 and the exposed portion 17. For example, the step ST3 is preferably performed by a semiconductor sheet forming apparatus included in the manufacturing apparatus. For example, in the step ST3, the semiconductor sheet 14 is transferred to the insulator 13 and the exposed portion 17 exposed from the opening 16 on the substrate 11.

Figure 12:
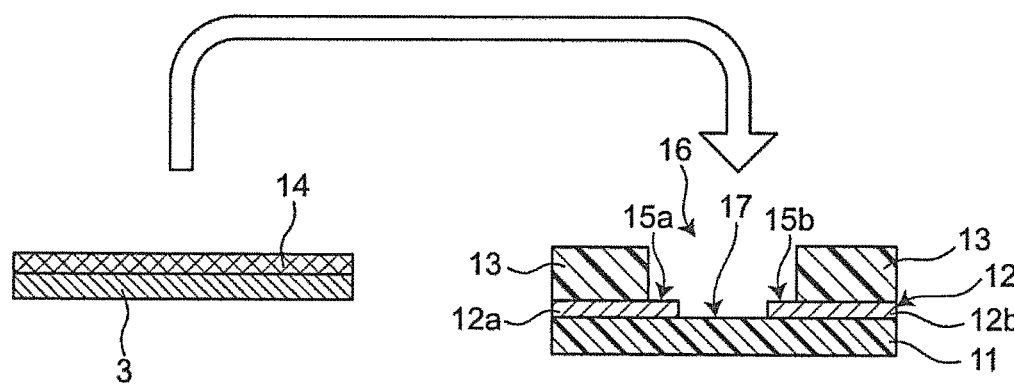
FIG. 12 is a diagram explaining an example of a process of forming a semiconductor sheet.

FIG. 12 is a diagram explaining an example of a process of forming the semiconductor sheet 14. FIG. 12 illustrates the process of forming the semiconductor sheet 14 by transfer. As illustrated in FIG. 12, the semiconductor sheet 14 formed on a base material 3 such as copper foil is moved onto the substrate 11 covered with the insulator 13.

The transfer of the semiconductor sheet 14 will be specifically described. First, for example, copper foil is prepared. The semiconductor sheet 14 is formed on a surface of the copper foil by, for example, a CVD device. PMMA is applied to a surface of the semiconductor sheet 14 as a graphene holding film. The copper foil provided with the semiconductor sheet 14 and the PMMA is floated on the surface of an etching solution that dissolves copper. Thus, the copper foil is dissolved, and the semiconductor sheet 14 whose surface is applied with the PMMA floats on the etching solution. The semiconductor sheet 14 floated on the etching solution is scooped up and placed on the substrate 11 on which the insulator 13 is formed. Thereafter, the PMMA is washed with a washing liquid.

Figure 7D:
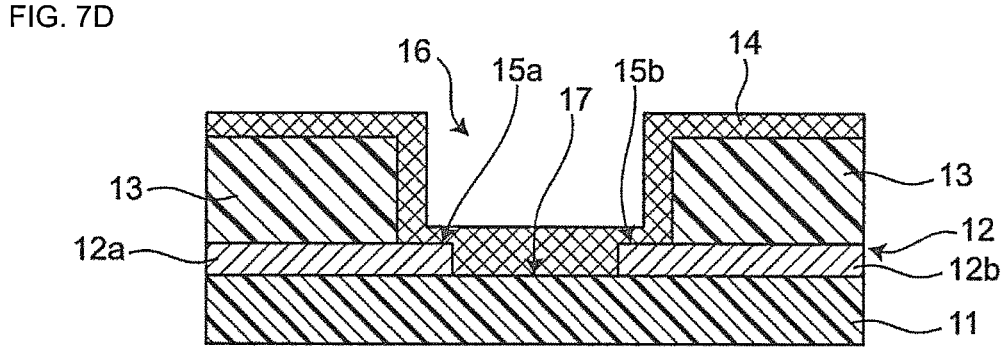
FIG. 7D is a schematic view illustrating an example of a process of the method of manufacturing the semiconductor device according to Preferred Embodiment 1 of the present invention.

As illustrated in FIG. 7D, when the semiconductor sheet 14 is transferred onto the upper surface of the insulator 13, the semiconductor sheet 14 is deformed by its own weight at the opening 16 and is provided on the exposed portion 17. At the exposed portion 17, the semiconductor sheet 14 is on a portion of the first electrode 12a and a portion of the second electrode 12b that are positioned at the exposed portion 17, and electrically connects the first electrode 12a and the second electrode 12b. After the semiconductor sheet 14 is transferred, the semiconductor sheet 14 is dried.

Figure 7E:
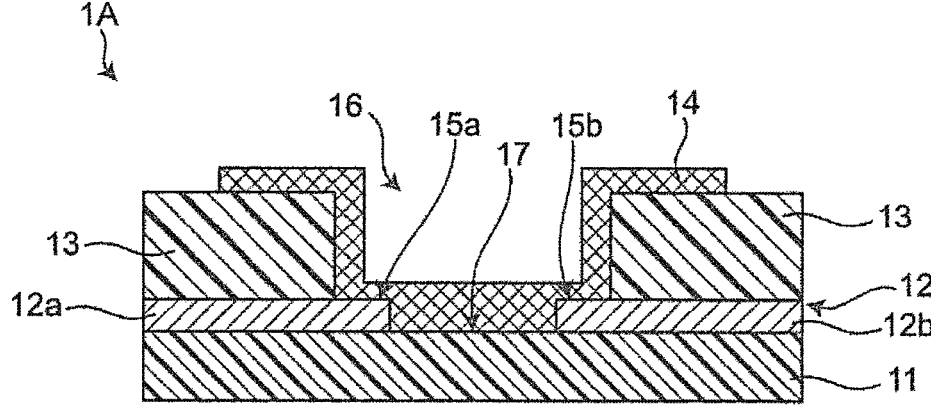
FIG. 7E is a schematic view illustrating an example of a process of the method of manufacturing the semiconductor device according to Preferred Embodiment 1 of the present invention.

Next, as illustrated in FIG. 7E, patterning is performed by removing a portion of the semiconductor sheet 14 on the insulator 13 by etching. In this way, the semiconductor device 1A is manufactured by performing the steps ST1 to ST3. The method of manufacturing the sensor 2 further includes a step of arranging the plurality of receptors 31 on the surface of the semiconductor sheet 14, in addition to the steps ST1 to ST3. In Preferred Embodiment 1, the example in which the semiconductor sheet 14 is formed by transfer in the step ST3 has been described, but the present invention is not limited thereto. For example, the semiconductor sheet 14 may be formed by sticking, growing, or coating.

Figure 13A:
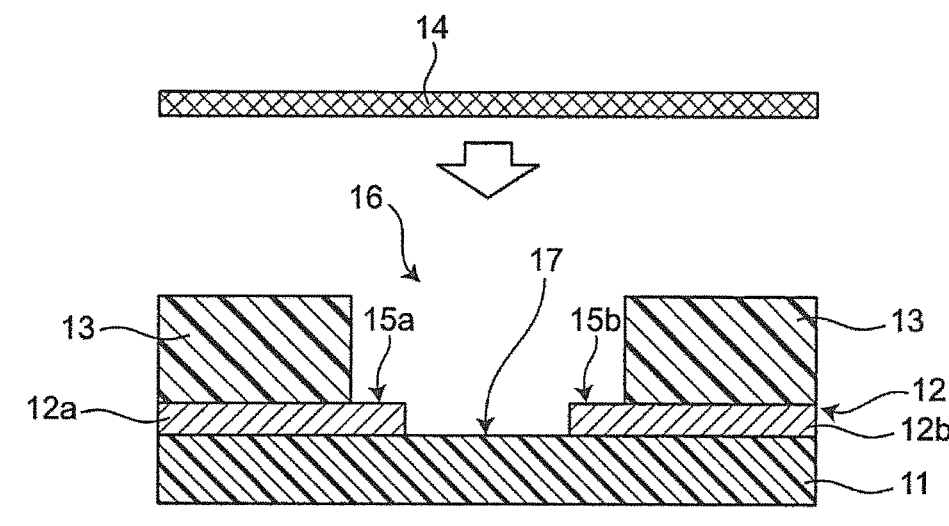
FIG. 13A is a diagram explaining another example of the process of forming the semiconductor sheet.
Figure 13B:
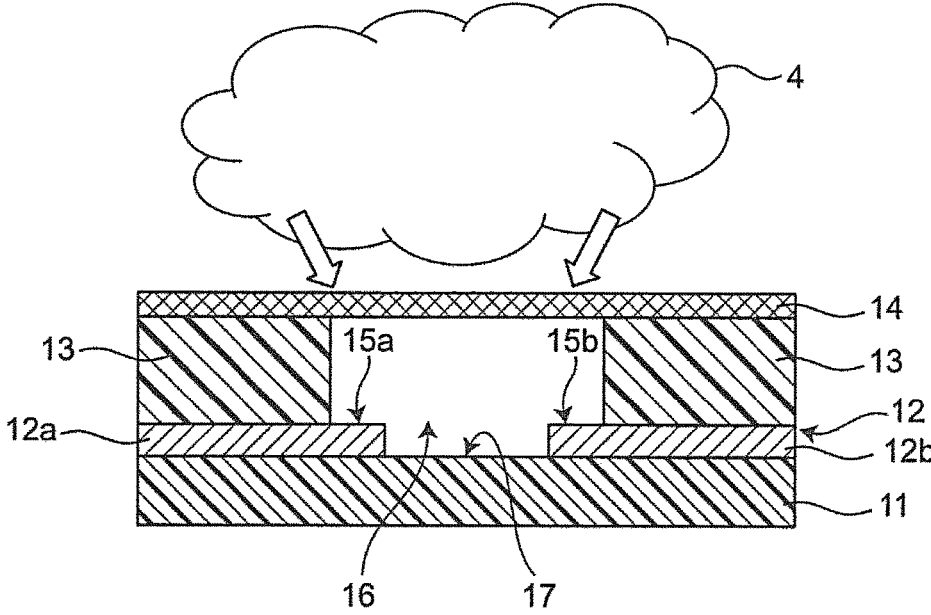
FIG. 13B is a diagram explaining still another example of the process of forming the semiconductor sheet.
Figure 13C:
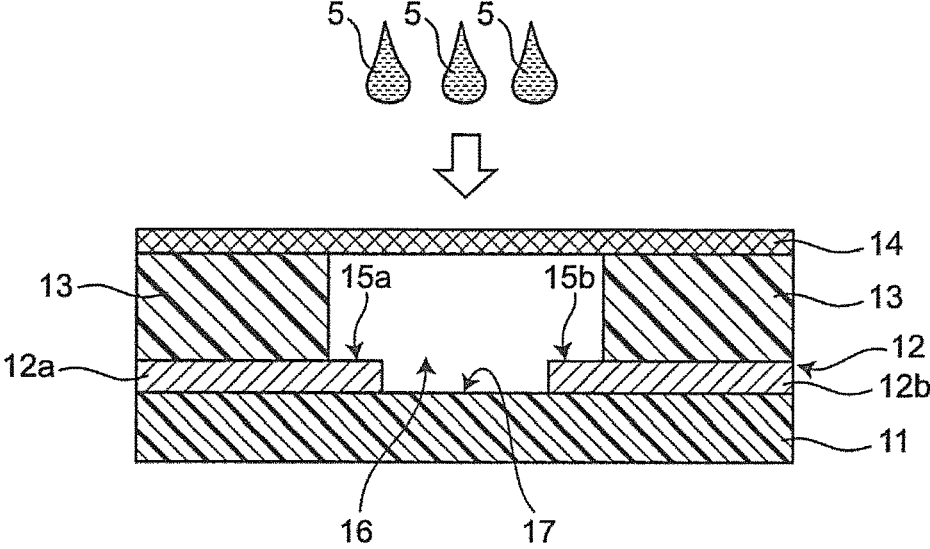
FIG. 13C is a diagram explaining still another example of the process of forming the semiconductor sheet.

FIGS. 13A to 13C are diagrams explaining other examples of the process of forming the semiconductor sheet 14. FIG. 13A illustrates an example of a process of forming the semiconductor sheet 14 by sticking. As illustrated in FIG. 13A, when the semiconductor sheet 14 is stable as a single body, the semiconductor sheet 14 may be pressed onto the substrate 11 covered with the insulator 13. FIG. 13B illustrates an example of a process of forming the semiconductor sheet 14 by growing. As illustrated in FIG. 13B, the semiconductor sheet 14 may be placed on the substrate 11 covered with the insulator 13 to be grown by using a reaction gas 4. FIG. 13C illustrates an example of a process of forming the semiconductor sheet 14 by coating. As illustrated in FIG. 13C, the semiconductor sheet 14 may be placed on the substrate 11 covered with the insulator 13, and then, may be applied with a liquid 5. The liquid 5 may be applied and then dried to form the semiconductor sheet 14.

In this way, in the step ST3, the semiconductor sheet 14 can be formed by a method such as transferring, sticking, growing, coating or the like.

With the semiconductor device 1A and the method of manufacturing the semiconductor device 1A according to Preferred Embodiment 1, the following advantageous effects can be obtained.

The semiconductor device 1A includes the substrate 11, the plurality of electrodes 12, the insulator 13, and the semiconductor sheet 14. The plurality of electrodes 12 are on the substrate 11. The insulator 13 is provided with the opening 16 exposing a portion of the plurality of electrodes 12 on the substrate 11. The insulator 13 exposes the portion of the plurality of electrodes 12 from the opening 16 and covers a portion of the plurality of electrodes 12. The semiconductor sheet 14 is on the insulator 13 and the exposed portion 17 exposed from the opening 16 on the substrate 11.

With such a configuration, it is possible to improve the performance of the semiconductor device 1A. In the semiconductor device 1A, since contamination on the surface of the semiconductor sheet 14 is reduced or prevented, deterioration in electrical characteristics of the semiconductor sheet 14 can be reduced or prevented. In addition, the plurality of receptors 31 and the like can be arranged on the surface of the semiconductor sheet 14 with high accuracy.

When the semiconductor device 1A is used as the sensor 2, the sensor 2 includes the plurality of receptors 31 arranged on the semiconductor sheet 14 and configured to capture a target molecule 50. With such a configuration, the target molecule 50 such as a virus can be captured. The semiconductor sheet 14 is also on the insulator 13 in addition to the exposed portion 17. This allows a plurality of receptors 31 to also be on the semiconductor sheet 14 arranged on the insulator 13. Thus, since a detection area of the target molecule 50 can be increased, the target molecule 50 can be easily captured.

The sensor 2 includes a calculator 32 configured to receive an electric signal output from the semiconductor sheet 14 and configured to calculate an amount of the target molecule 50 based on the electric signal. With such a configuration, it is possible to calculate the amount of the target molecule 50, to determine the presence or absence of the target molecule 50, and/or to calculate a concentration thereof.

The semiconductor sheet 14 is in close contact with the insulator 13 and the exposed portion 17 by van der Waals force. With such a configuration, the semiconductor sheet 14 can be easily fixed to the insulator 13 and the exposed portion 17. In addition, since it is not necessary to use an adhesive or the like, the cost can be reduced.

The method of manufacturing the semiconductor device 1A includes the step ST1 of preparing the substrate 11, the step ST2 of forming the insulator 13, and the step ST3 of forming the semiconductor sheet 14. In the step ST1, the substrate 11 on which the plurality of electrodes 12 are provided is prepared. In the step ST2, the insulator 13 provided with the opening 16 exposing a portion of the plurality of electrodes 12 on the substrate 11, the insulator 13 covering a portion of the plurality of electrodes 12, is formed. In the step ST3, the semiconductor sheet 14 is formed on the insulator 13 and the exposed portion 17 exposed from the opening 16 on the substrate 11. With this configuration, it is possible to manufacture the semiconductor device 1A having improved performance. According to the method of manufacturing, since the semiconductor sheet 14 is formed after the insulator 13 is formed, contaminating the surface of the semiconductor sheet 14 can be reduced or prevented.

In Preferred Embodiment 1, the example in which the semiconductor device 1A is the field effect transistor including the electrolyte solution 20 has been described, but the present invention is not limited thereto. The semiconductor device 1A may be any device provided with the semiconductor sheet 14. Examples of other devices include cyclic voltammetry elements, semiconductor heterojunction devices and the like.

In Preferred Embodiment 1, the example in which the semiconductor device 1A is the sensor 2 that is a biosensor to detect a virus has been described, but the present invention is not limited thereto. For example, the semiconductor device 1A may be used as a sensor such as a chemical sensor to detect an ion.

In Preferred Embodiment 1, the example in which the plurality of electrodes 12 are covered with the insulator 13 provided with the opening 16 exposing the plurality of electrodes on the substrate 11 has been described, but the present invention is not limited thereto. For example, the insulator 13 may cover at least a portion of the plurality of electrodes 12.

In Preferred Embodiment 1, the example in which the opening 16 exposes the plurality of electrodes 12 has been described, but the present invention is not limited thereto. For example, the opening 16 may expose at least one electrode among the plurality of electrodes 12 on the substrate 11.

In Preferred Embodiment 1, the example in which the region 15a including the end portion of the first electrode 12a opposing the second electrode 12b and the region 15b including the end portion of the second electrode 12b opposing the first electrode 12a are positioned at the exposed portion 17 has been described, but the present invention is not limited thereto. At least one of a portion of the first electrode 12a and a portion of the second electrode 12b may be positioned at the exposed portion 17.

In Preferred Embodiment 1, the example in which one opening 16 is provided in the insulator 13 for one set of electrode patterns including the first electrode 12a and the second electrode 12b has been described, but the present invention is not limited thereto. For example, the insulator 13 may be provided with one or a plurality of openings 16 of the one set of electrode patterns.

In Preferred Embodiment 1, the example in which one opening 16 exposing the first electrode 12a and the second electrode 12b is formed of the one set of electrode patterns including the first electrode 12a and the second electrode

12b has been described, but the present invention is not limited thereto. For example, one or a plurality of openings 16 may be formed of the one set of electrode patterns.

In Preferred Embodiment 1, the example in which the opening 16 is formed in a rectangular shape when the semiconductor device 1A is viewed from the height direction (Z direction) has been described, but the present invention is not limited thereto. For example, the opening 16 may be circular, elliptical, or polygonal.

In Preferred Embodiment 1, the steps ST1 to ST3 illustrated in FIG. 6 have been described as an example of the method of manufacturing the semiconductor device 1A, but the present invention is not limited thereto. For example, the steps ST1 to ST3 illustrated in FIG. 6 may be integrated or divided. Alternatively, the flowchart illustrated in FIG. 6 may include an additional step. For example, a step of preprocessing the substrate 11 before forming the semiconductor sheet 14, a step of drying the semiconductor sheet 14, a step of etching the semiconductor sheet 14, and the like may be added.

In Preferred Embodiment 1, the step ST2 of forming the insulator 13 has been described using the example of the processes illustrated in FIGS. 7A to 7E, but the present invention is not limited thereto. For example, in the step ST2, the insulator 13 may be formed by using a resist. In Preferred Embodiment 1, the example in which the opening 16 is provided by photolithography in the step ST2 has been described, but the present invention is not limited thereto. The opening 16 may be provided by a method other than the photolithography.

Figure 14:
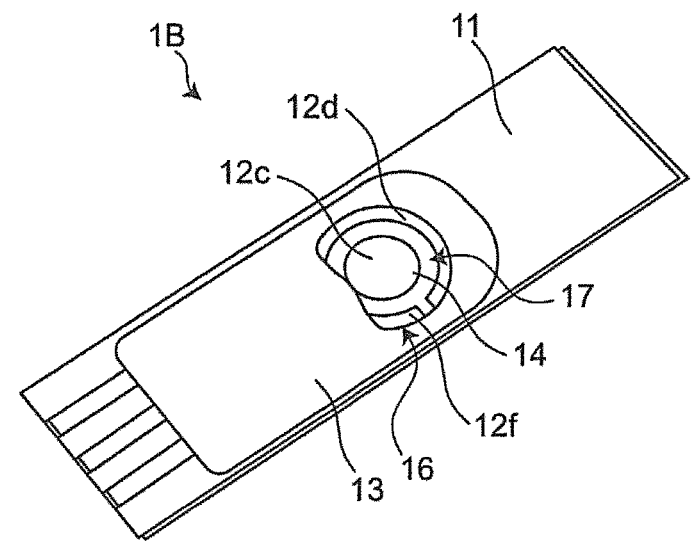
FIG. 14 is a schematic perspective view of a semiconductor device according to a modification of Embodiment 1 of the present invention.

FIG. 14 is a schematic perspective view of a semiconductor device 1B according to a modification of Preferred Embodiment 1 of the present invention. The semiconductor device 1B illustrated in FIG. 14 is a device to detect a virus by cyclic voltammetry. As illustrated in FIG. 14, the semiconductor device 1B includes a working electrode 12c, a counter electrode 12d, and a reference electrode 12f as a plurality of electrodes 12. In the semiconductor device 1B, the working electrode 12c, the counter electrode 12d, and the reference electrode 12f are provided on the substrate 11. The counter electrode 12d and the reference electrode 12f are covered with the insulator 13 provided with the opening 16. The opening 16 exposes the working electrode 12c, a portion of the counter electrode 12d, and a portion of the reference electrode 12f. The semiconductor sheet 14 is formed on a surface of the working electrode 12c. In this manner, the semiconductor sheet 14 may be on one electrode among the plurality of electrodes 12.

Preferred Embodiment 2

A method of manufacturing a semiconductor device according to Preferred Embodiment 2 of the present invention will be described.

In Preferred Embodiment 2, differences from Preferred Embodiment 1 will be primarily described. In Preferred Embodiment 2, configurations identical or equivalent to those in Preferred Embodiment 1 will be denoted by the same reference signs and described. Additionally, in Preferred Embodiment 2, the description overlapping with Preferred Embodiment 1 will be omitted. Preferred Embodiment 2 is different from Preferred Embodiment 1 in that a resist is preferably used in the step ST2 of forming an insulator.

A method of manufacturing the semiconductor device 1A according to Preferred Embodiment 2 will be described with reference to FIGS. 15A to 15F. FIGS. 15A to 15F are schematic views illustrating an example of processes of the method of manufacturing the semiconductor device 1A according to Preferred Embodiment 2 of the present invention. A flowchart of the method of manufacturing according to Preferred Embodiment 2 is the same as or similar to the flowchart illustrated in FIG. 6 of Preferred Embodiment 1.

Figure 15A:
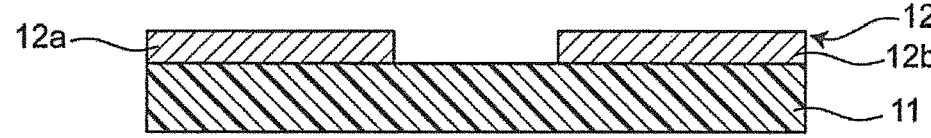
FIG. 15A is a schematic view illustrating an example of a process of a method of manufacturing a semiconductor device according to Preferred Embodiment 2 of the present invention.
Figure 15B:
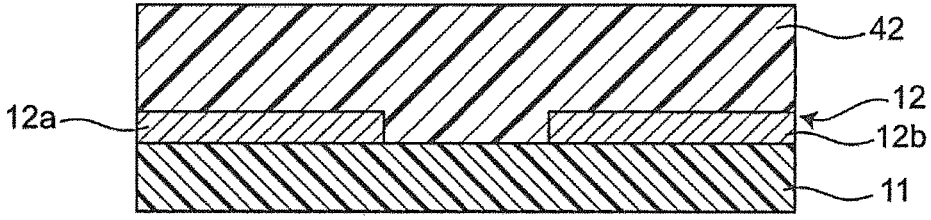
FIG. 15B is a schematic view illustrating an example of a process of the method of manufacturing the semiconductor device according to Preferred Embodiment 2 of the present invention.

In the step ST1, as illustrated in FIG. 15A, the substrate 11 on which the plurality of electrodes 12 are provided is prepared. In the step ST2, the insulator 13 provided with the opening 16 is formed on the substrate 11 on which the plurality of electrodes 12 are provided. As illustrated in FIG. 15B, a resist film 42 is formed by applying a resist on the substrate 11 and drying the resist.

Figure 15C:
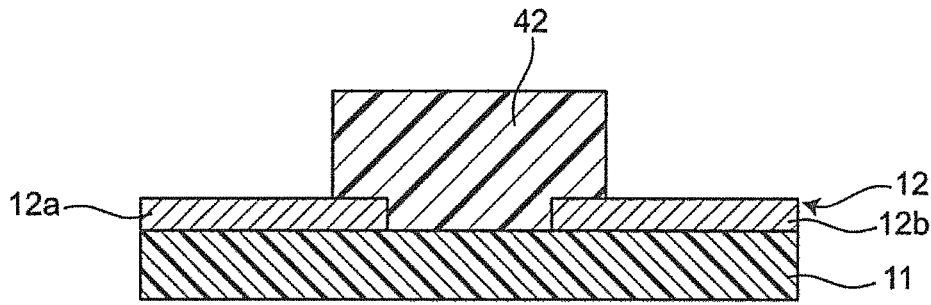
FIG. 15C is a schematic view illustrating an example of a process of the method of manufacturing the semiconductor device according to Preferred Embodiment 2 of the present invention.

As illustrated in FIG. 15C, a portion of the resist film 42 is removed by, for example, photolithography. Specifically, the resist film 42 corresponding to a portion where the insulator 13 is to be formed is preferably removed by the photolithography while the resist film 42 corresponding to a position where the opening 16 is to be provided remains on the substrate 11. For example, the resist film 42 covering the first electrode 12a and the second electrode 12b is removed while the resist film 42 in a portion across the first electrode 12a and the second electrode 12b remains on the substrate 11.

Figure 15D:
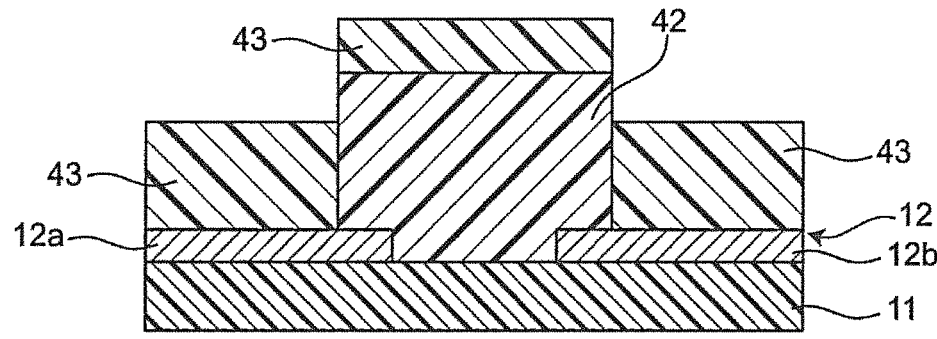
FIG. 15D is a schematic view illustrating an example of a process of the method of manufacturing the semiconductor device according to Preferred Embodiment 2 of the present invention.

As illustrated in FIG. 15D, an insulating coating material 43 is film-formed on the substrate 11. Thus, the first electrode 12a and the second electrode 12b on the substrate 11 are covered with the insulating coating material 43.

Figure 15E:
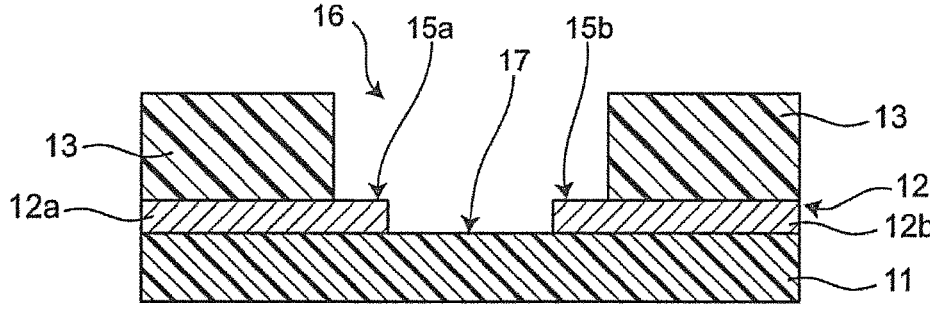
FIG. 15E is a schematic view illustrating an example of a process of the method of manufacturing the semiconductor device according to Preferred Embodiment 2 of the present invention.

As illustrated in FIG. 15E, the resist film 42 is removed by, for example, lift-off. The opening 16 is formed at a portion where the resist film 42 is removed. Thus, the insulator 13 provided with the opening 16 is formed. A portion of the plurality of electrodes 12 is positioned at the exposed portion 17 exposed from the opening 16 on the substrate 11. In Preferred Embodiment 2, the region 15a including an end portion of the first electrode 12a opposing the second electrode 12b and the region 15b including an end portion of the second electrode 12b opposing the first electrode 12a are positioned at the exposed portion 17.

Figure 15F:
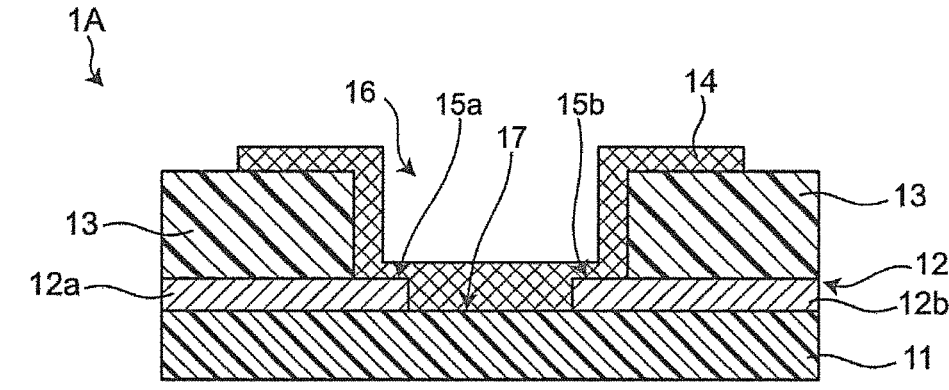
FIG. 15F is a schematic view illustrating an example of a process of the method of manufacturing the semiconductor device according to Preferred Embodiment 2 of the present invention.

In the step ST3, as illustrated in FIG. 15F, the semiconductor sheet 14 is formed on the insulator 13 and the exposed portion 17. For example, the semiconductor sheet 14 can be formed by transferring, sticking, growing, or coating.

As described above, in the step ST2, the insulator 13 provided with the opening 16 can be formed using the resist film 42.

With the method of manufacturing the semiconductor device 1A according to Preferred Embodiment 2, the following advantageous effects can be obtained.

In the method of manufacturing the semiconductor device 1A according to Preferred Embodiment 2, in the step ST2 of forming the insulator 13, the insulator 13 provided with the opening 16 is preferably formed on the substrate 11 by using the resist film 42. Specifically, the resist film 42 is at a position where the opening 16 is provided, and the insulating coating material 43 is film-formed on the resist film 42. Thereafter, the resist film 42 is removed. Thus, the insulator 13 provided with the opening 16 can be easily formed.

Further, unlike Preferred Embodiment 1, it is not necessary to remove a portion of the insulating coating material by the photolithography in the method of manufacturing according to Preferred Embodiment 2, and thus, a range of selection of an insulator material to be used for the insulating coating material 43 forming the insulator 13 is widened as compared with Preferred Embodiment 1. For example, it is possible to use the insulating coating material 43 that is more excellent in insulating property and/or water resistance than the insulating coating material 41 according to Preferred Embodiment 1.

In Preferred Embodiment 2, the example in which a portion of the resist film 42 is removed by the photolithography has been described, but the present invention is not limited thereto. The resist film 42 may be removed by a method other than the photolithography.

Preferred Embodiment 3

A method of manufacturing a semiconductor device according to Preferred Embodiment 3 of the present invention will be described.

In Preferred Embodiment 3, differences from Preferred Embodiment 1 will be primarily described. In Preferred Embodiment 3, configurations identical or equivalent to those in Preferred Embodiment 1 will be denoted by the same reference signs and described. Additionally, in Preferred Embodiment 3, the description overlapping with Preferred Embodiment 1 will be omitted.

Preferred Embodiment 3 is different from Preferred Embodiment 1 in that a resist is preferably used and an opening is formed by etching in the step ST2 of forming an insulator.

A method of manufacturing the semiconductor device 1A according to Preferred Embodiment 3 will be described with reference to FIGS. 16A to 16G. FIGS. 16A to 16G are schematic views illustrating an example of processes of the method of manufacturing the semiconductor device 1A according to Preferred Embodiment 3 of the present invention. A flowchart of the method of manufacturing according to Preferred Embodiment 3 is the same as or similar to the flowchart illustrated in FIG. 6 of Preferred Embodiment 1.

Figure 16A:
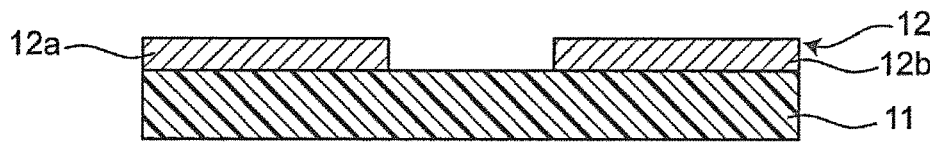
FIG. 16A is a schematic view illustrating an example of a process of a method of manufacturing a semiconductor device according to Preferred Embodiment 3 of the present invention.
Figure 16B:
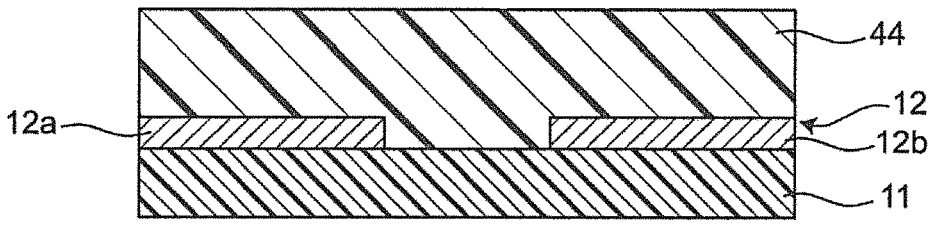
FIG. 16B is a schematic view illustrating an example of a process of the method of manufacturing the semiconductor device according to Preferred Embodiment 3 of the present invention.
Figure 16C:
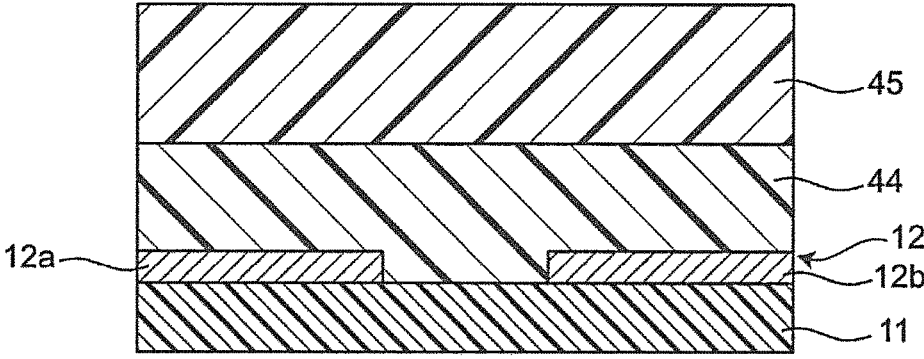
FIG. 16C is a schematic view illustrating an example of a process of the method of manufacturing the semiconductor device according to Preferred Embodiment 3 of the present invention.

In the step ST1, as illustrated in FIG. 16A, the substrate 11 on which the plurality of electrodes 12 are provided is prepared. In the step ST2, the insulator 13 is formed on the substrate 11 on which the plurality of electrodes 12 are provided. As illustrated in FIG. 16B, an insulating coating material 44 is film-formed on the substrate 11. As illustrated in FIG. 16C, a resist film 45 is formed on the insulating coating material 44.

Figure 16D:
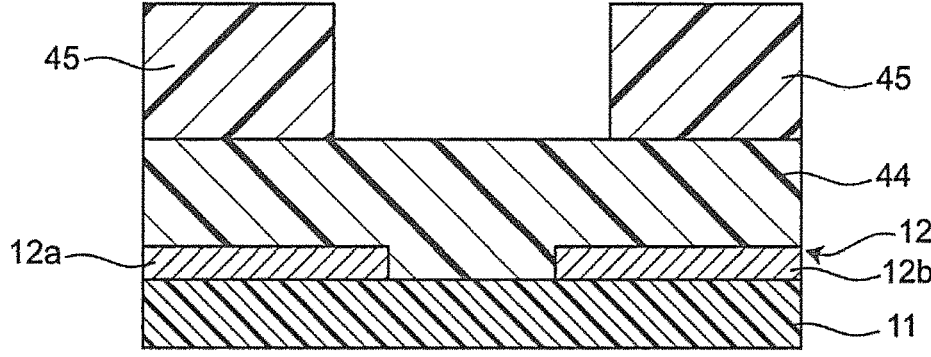
FIG. 16D is a schematic view illustrating an example of a process of the method of manufacturing the semiconductor device according to Preferred Embodiment 3 of the present invention.

As illustrated in FIG. 16D, a portion of the resist film 45 is removed by, for example, photolithography. Specifically, by the photolithography, the resist film 45 corresponding to a portion where the opening 16 is provided is removed while the resist film 45 on the insulating coating material 44 corresponding to a portion where a coating portion 15 is formed remains. For example, the resist film 45 on the insulating coating material 44 extending across the first electrode 12a and the second electrode 12b is removed while the resist film 42 on the insulating coating material 44 covering the first electrode 12a and the second electrode 12b remains.

Figure 16E:
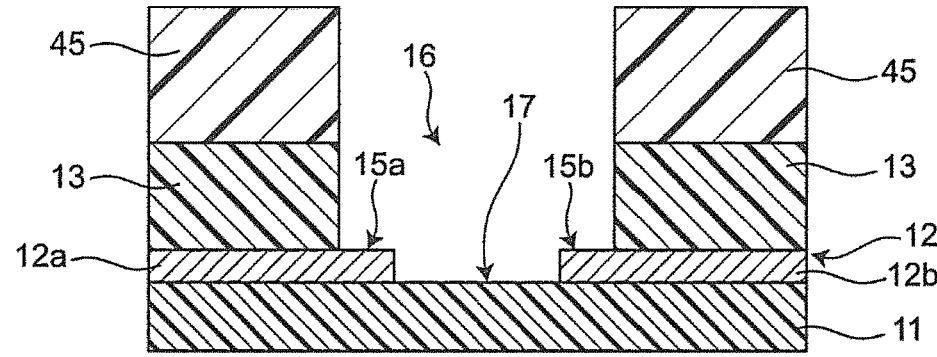
FIG. 16E is a schematic view illustrating an example of a process of the method of manufacturing the semiconductor device according to Preferred Embodiment 3 of the present invention.

As illustrated in FIG. 16E, the insulating coating material 44 in the portion where the resist film 45 has been removed is removed by etching. Thus, the opening 16 is formed. A portion of the plurality of electrodes 12 is positioned at the exposed portion 17 exposed by the opening 16 on the substrate 11. In Preferred Embodiment 3, the region 15a including an end portion of the first electrode 12a opposing the second electrode 12b and the region 15b including an end portion of the second electrode 12b opposing the first electrode 12a are positioned at the exposed portion 17.

Figure 16F:
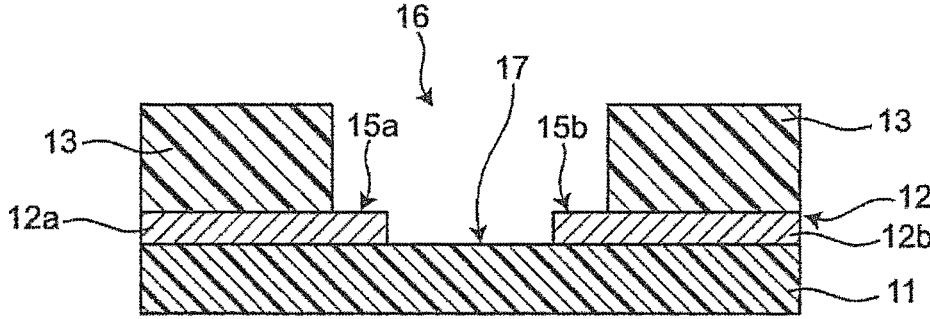
FIG. 16F is a schematic view illustrating an example of a process of the method of manufacturing the semiconductor device according to Preferred Embodiment 3 of the present invention.

As illustrated in FIG. 16F, the resist film 45 is removed. Thus, the insulator 13 provided with the opening 16 is formed.

Figure 16G:
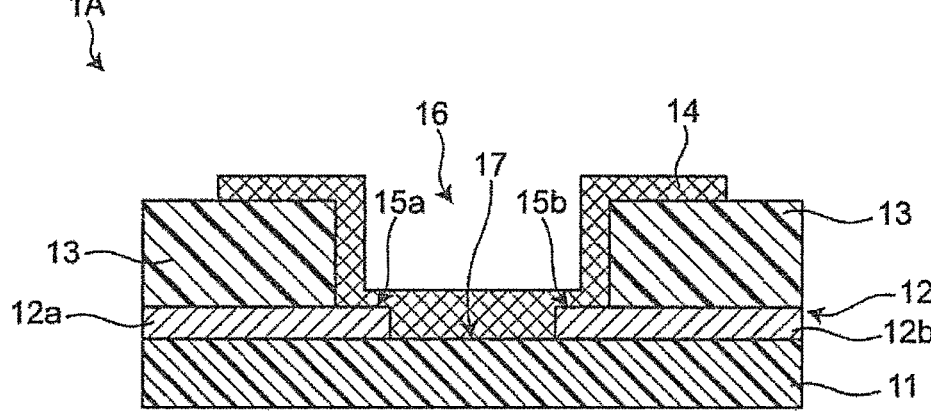
FIG. 16G is a schematic view illustrating an example of a process of the method of manufacturing the semiconductor device according to Preferred Embodiment 3 of the present invention.

In the step ST3, as illustrated in FIG. 16G, the semiconductor sheet 14 is formed on the insulators 13 and the exposed portions 17. For example, the semiconductor sheet 14 can be formed by transferring, sticking, growing, or coating.

As described above, in the step ST2, the resist film 45 is formed on the insulating coating material 44, and a portion of the insulating coating material 44 is removed by etching, thus forming the insulator 13 provided with the opening 16.

With the method of manufacturing the semiconductor device 1A according to Preferred Embodiment 3, the following advantageous effects can be obtained.

In the method of manufacturing the semiconductor device 1A according to Preferred Embodiment 3, in the step ST2 of forming the insulator 13, the insulator 13 provided with the opening 16 is formed using the resist film 45. Specifically, the resist film 45 is formed on the insulating coating material 44, and a portion of the resist film 45 corresponding to a portion where the opening 16 is provided is removed. Then, the portion of the insulating coating material 44 from which the resist film 45 has been removed is removed by etching. Thus, the insulator 13 provided with the opening 16 can be easily formed.

In addition, in the method of manufacturing according to Preferred Embodiment 3, since the opening 16 is formed by etching, a range of selection of the material to be used for the insulating coating material 44 is widened as compared with Preferred Embodiment 1. For example, it is possible to use the insulating coating material 44 that is more excellent in insulating property and/or water resistance than the insulating coating material 41 according to Preferred Embodiment 1.

Preferred Embodiment 4

A semiconductor device and a method of manufacturing a semiconductor device according to Preferred Embodiment 4 of the present invention will be described. In Preferred Embodiment 4, differences from Preferred Embodiment 1 will be primarily described. In Preferred Embodiment 4, configurations identical or equivalent to those in Preferred Embodiment 1 will be denoted by the same reference signs and described. Additionally, in Preferred Embodiment 4, the description overlapping with Preferred Embodiment 1 will be omitted.

Preferred Embodiment 4 is different from Preferred Embodiment 1 in that an insulator includes a coupling insulating portion extending across a first electrode and a second electrode, a first opening exposing the first electrode and a second opening exposing the second electrode are provided in the insulator, and a semiconductor sheet is continuously provided on the coupling insulating portion, a first exposed portion exposed from the first opening, and a second exposed portion exposed from the second opening.

Figure 17:
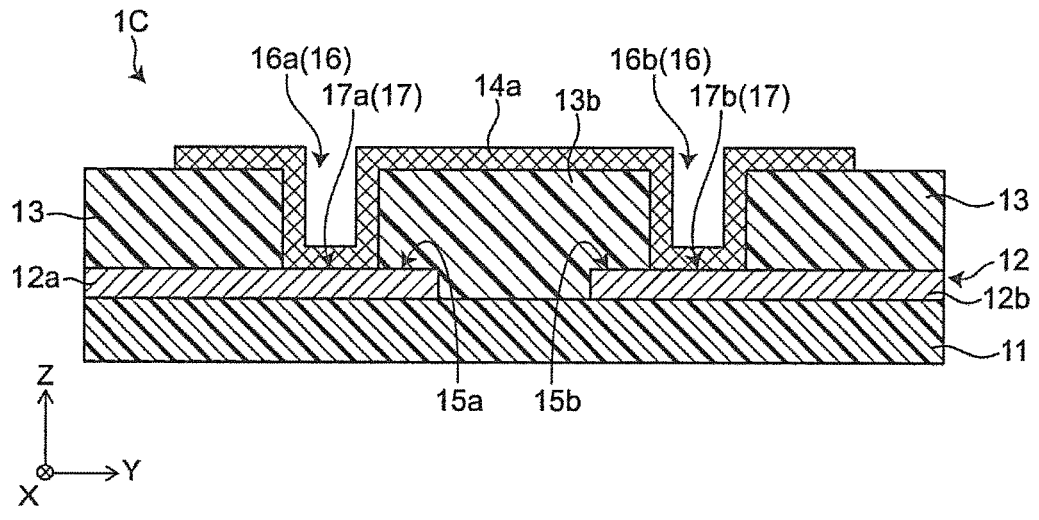
FIG. 17 is a schematic view illustrating an example of a main configuration of a semiconductor device according to Preferred Embodiment 4 of the present invention.
Figure 18:
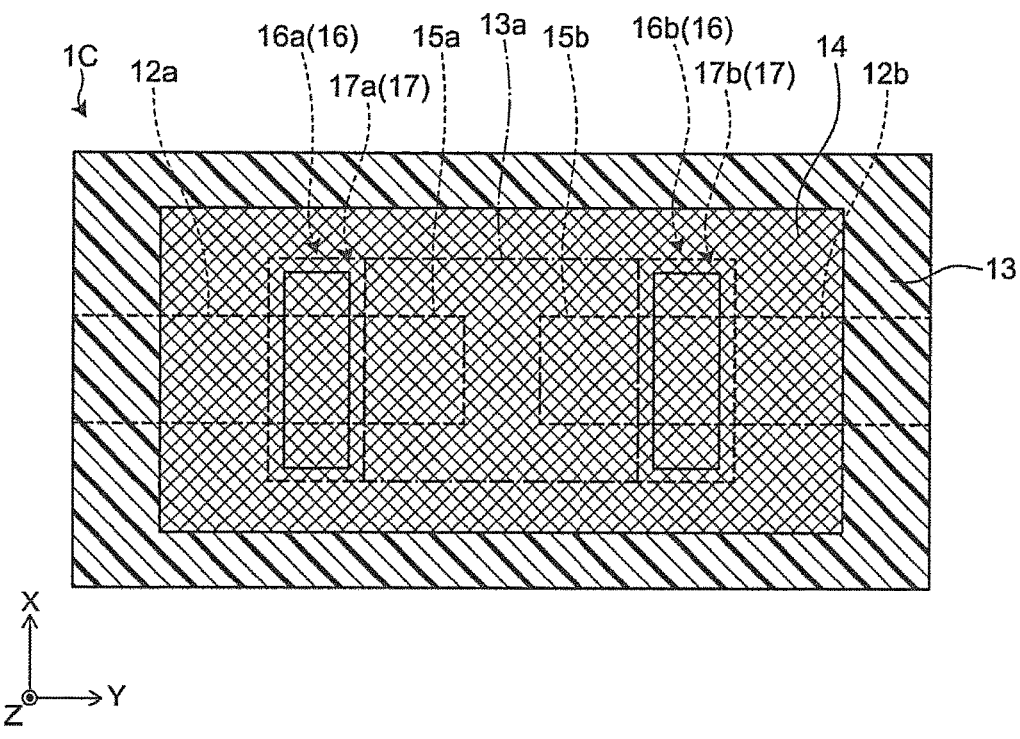
FIG. 18 is a schematic plan view illustrating an example of a main configuration of the semiconductor device according to Preferred Embodiment 4 of the present invention.

A semiconductor device 1C according to Preferred Embodiment 4 will be described with reference to FIG. 17 and FIG. 18. FIG. 17 is a schematic diagram illustrating an example of a main configuration of the semiconductor device 1C according to Preferred Embodiment 4 of the present invention. FIG. 18 is a schematic plan view illustrating an example of a main configuration of the semiconductor device 1C according to Preferred Embodiment 4 of the present invention.

As illustrated in FIG. 17 and FIG. 18, the insulator 13 includes a coupling insulating portion 13b disposed across the first electrode 12a and the second electrode 12b on the substrate 11. To be specific, the coupling insulating portion 13b is on a portion of the substrate 11, a portion of the first electrode 12a, and a portion of the second electrode 12b. In Preferred Embodiment 4, the coupling insulating portion 13b is provided across the region 15a including an end portion of the first electrode 12a opposing the second electrode 12b and the region 15b including an end portion of the second electrode 12b opposing the first electrode 12a.

The insulator 13 includes a plurality of openings 16. The plurality of openings 16 include a first opening 16a and a second opening 16b. The coupling insulating portion 13b is a portion separating the first opening 16a and the second opening 16b in the insulator 13. Both side walls of the coupling insulating portion 13b individually define the first opening 16a and the second opening 16b.

In Preferred Embodiment 4, as illustrated in FIG. 18, the first opening 16a and the second opening 16b are formed in a rectangular shape when the semiconductor device 1C is viewed from a height direction (Z direction). The first opening 16a exposes a portion of the substrate 11 and a portion of the first electrode 12a. The second opening 16b exposes a portion of the substrate 11 and a portion of the second electrode 12b.

A plurality of exposed portions 17 exposed by the plurality of openings 16a and 16b are formed on the substrate 11. A first exposed portion 17a is a portion exposed from the first opening 16a on the substrate 11. A second exposed portion 17b is a portion exposed from the second opening 16b on the substrate 11.

In Preferred Embodiment 4, a portion of the first electrode 12a is positioned at the first exposed portion 17a. A portion of the second electrode 12b is positioned at the second exposed portion 17b.

A semiconductor sheet 14a is continuously provided on the coupling insulating portion 13b, the first exposed portion 17a, and the second exposed portion 17b. Here, "continuously provided" means that the semiconductor sheet 14 is provided with all portions being connected. That is, one semiconductor sheet 14a covers the coupling insulating portion 13b, the first exposed portion 17a, and the second exposed portion 17b. The semiconductor sheet 14a electrically connects the first electrode 12a positioned at the first exposed portion 17a and the second electrode 12b positioned at the second exposed portion 17b.

Figure 19:
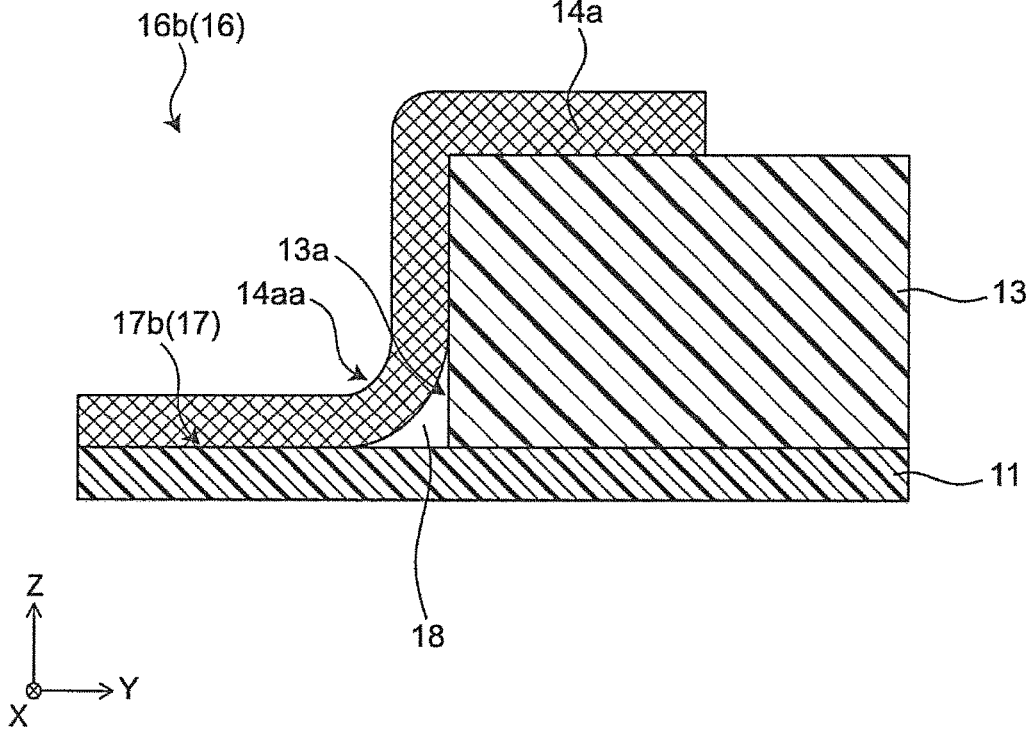
FIG. 19 is a schematic enlarged view in which a portion of an exposed portion is enlarged.

FIG. 19 is a schematic enlarged view in which a portion of the exposed portion 17 is enlarged. FIG. 19 is an enlarged view of the vicinity of a portion where the substrate 11 positioned at the second exposed portion 17b and the insulator 13 are connected to each other. As illustrated in FIG. 19, a gap 18 is provided between a side wall 13a of the insulator 13 provided with the second opening 16b, the semiconductor sheet 14a, and the substrate 11. The "side wall 13a of the insulator 13 provided with the second opening 16b" means the side wall 13a of the insulator 13 defining the second opening 16b. To be specific, the semiconductor sheet 14a preferably includes a bent portion 14aa bent in an arc shape at a corner portion where the side wall 13a of the insulator 13 defining the second opening 16b and the surface of the substrate 11 are connected.

In the second opening 16b, the semiconductor sheet 14a extends from an upper surface of the insulator 13 along the side wall 13a. The semiconductor sheet 14a extending along the side wall 13a of the insulator 13 extends toward the substrate 11. At the corner portion where the side wall 13a of the insulator 13 and the surface of the substrate 11 are connected to each other, the semiconductor sheet 14a is bent by the bent portion 14aa and extends in a direction away from the side wall 13a. The semiconductor sheet 14a then extends on the surface of the substrate 11.

In the example illustrated in FIG. 19, the second exposed portion 17b has been described as an example, but the present invention is not limited thereto. The first exposed portion 17a may have a similar configuration. That is, the gap 18 may be provided between the side wall 13a of the insulator 13 provided with the first opening 16a, the semiconductor sheet 14a, and the substrate 11.

Additionally, the side wall 13a of the insulator 13 may be a side wall of the coupling insulating portion 13b. In Preferred Embodiment 4, the side walls of the coupling insulating portion 13b define the first opening 16a and the second opening 16b. For this reason, the gap 18 may be formed between the side wall of the coupling insulating portion 13b provided with the first opening 16a, the semiconductor sheet 14a, and the substrate 11. Alternatively, the gap 18 may be provided between the side wall of the coupling insulating portion 13b provided with the second opening 16b, the semiconductor sheet 14a, and the substrate 11.

Method of Manufacturing

Figure 20:
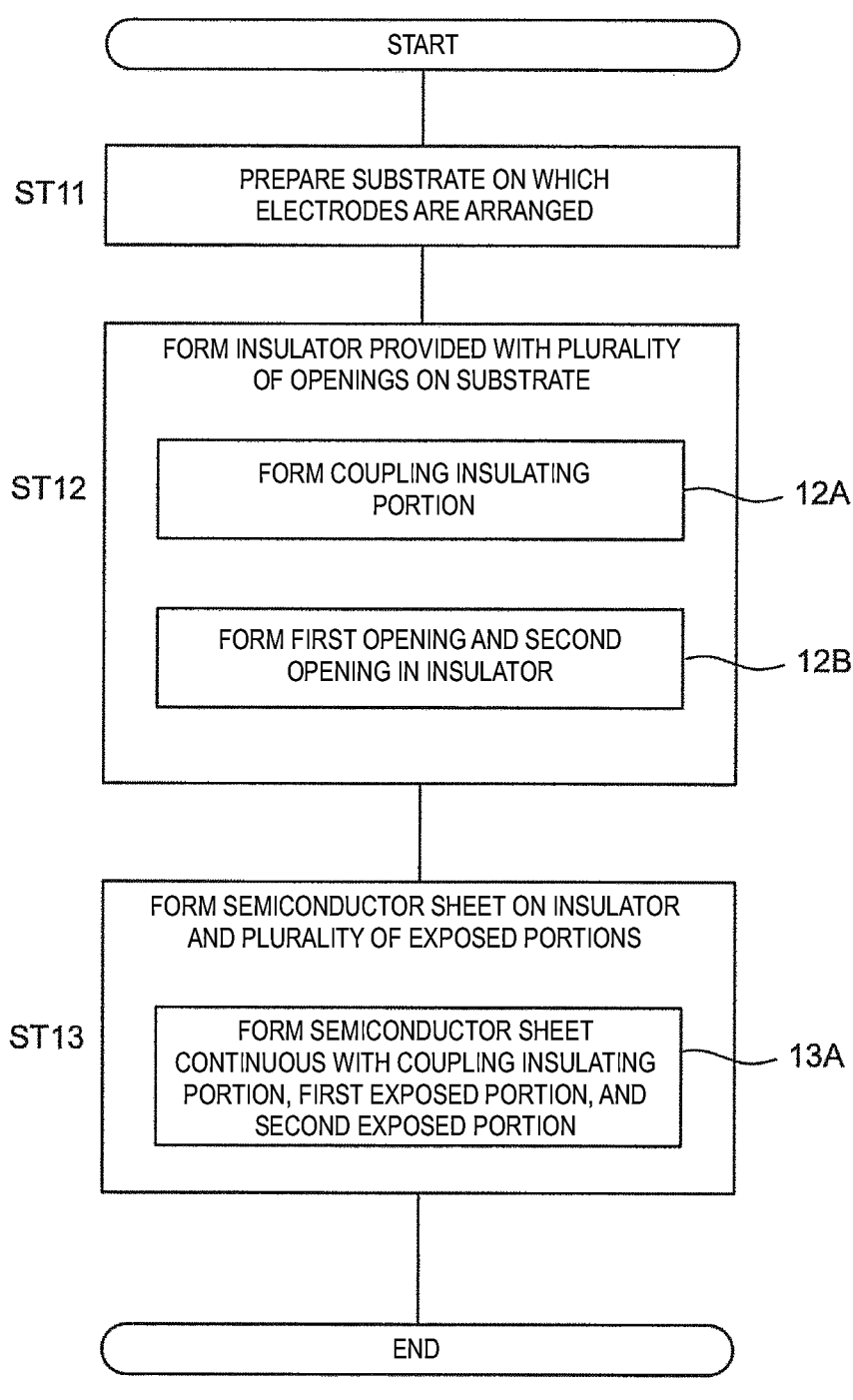
FIG. 20 is a flowchart of an example of a method of manufacturing the semiconductor device according to Preferred Embodiment 4 of the present invention.
Figure 21A:
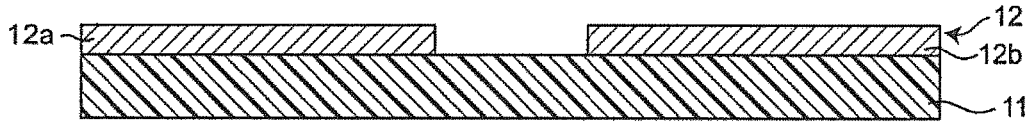
FIG. 21A is a schematic view illustrating an example of a process of the method of manufacturing the semiconductor device according to Preferred Embodiment 4 of the present invention.

An example of a method of manufacturing the semiconductor device 1C will be described. FIG. 20 is a flowchart of an example of the method of manufacturing the semiconductor device 1C according to Preferred Embodiment 4 of the present invention. FIGS. 21A 21D are schematic views illustrating an example of processes of the method of manufacturing the semiconductor device 1C according to Preferred Embodiment 4 of the present invention. Steps that will be described below are executed by a manufacturing apparatus. Since a step ST11 is the same as or similar to the step ST1 illustrated in FIG. 6 of Preferred Embodiment 1, detailed description thereof will be omitted.

As illustrated in FIG. 20 and FIG. 21A, in the step ST11, the substrate 11 on which the plurality of electrodes 12 are provided is prepared. For example, the step ST11 is preferably performed by a metal film forming apparatus represented by, for example, a sputtering apparatus or an electron beam (EB) vapor deposition apparatus included in the manufacturing apparatus.

In a step ST12, the insulator 13 including a plurality of openings 16 is formed on the substrate 11. To be specific, in the step ST12, the insulator 13 provided with the first opening 16a exposing a portion of the first electrode 12a and the second opening 16b exposing a portion of the second electrode 12b is formed on the substrate 11. The insulator 13 exposes a portion of the first electrode 12a and a portion of the second electrode 12b from the first opening 16a and the second opening 16b, respectively, and covers a portion of the first electrode 12a and a portion of the second electrode 12b. For example, the step ST12 is performed by an insulating film forming apparatus represented by a spin coater, various vapor deposition apparatuses, and a CVD apparatus, and a photolithography apparatus that are included in the manufacturing apparatus.

The step ST12 includes a step ST12A of forming the coupling insulating portion 13b and a step ST12B of forming the first opening 16a and the second opening 16b.

In the step ST12A of forming the coupling insulating portion 13b, the coupling insulating portion 13b disposed across the first electrode 12a and the second electrode 12b is formed.

In the step ST12B of forming the first opening 16a and the second opening 16b, the first opening 16a exposing a portion of the first electrode 12a on the substrate 11 and the second opening 16b exposing a portion of the second electrode 12b on the substrate 11 are formed in the insulator 13.

The step ST12A and the step ST12B may be integrated, or the order thereof may be changed. The coupling insulating portion 13b, the first opening 16a, and the second opening 16b can be formed by a method the same as or similar to that in the step ST2 of forming the insulator 13 in Preferred Embodiments 1 to 3. For example, the coupling insulating portion 13b, the first opening 16a, and the second opening 16b can be formed by film-forming an insulating coating material on the substrate 11 and performing photolithography.

Figure 21B:
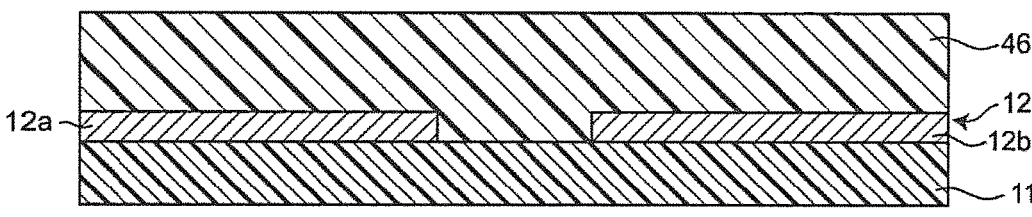
FIG. 21B is a schematic view illustrating an example of a process of the method of manufacturing the semiconductor device according to Preferred Embodiment 4 of the present invention.
Figure 21C:
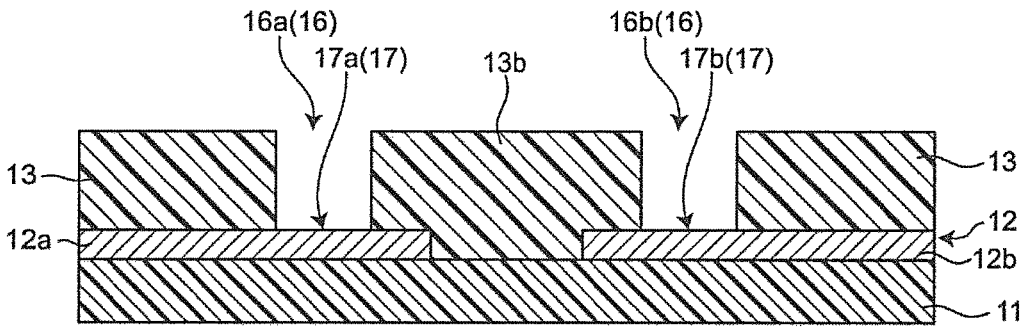
FIG. 21C is a schematic view illustrating an example of a process of the method of manufacturing the semiconductor device according to Preferred Embodiment 4 of the present invention.
Figure 21D:
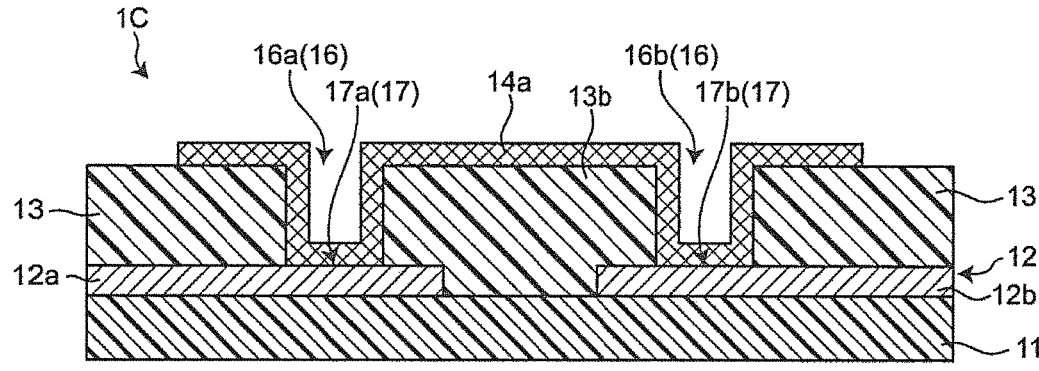
FIG. 21D is a schematic view illustrating an example of a process of the method of manufacturing the semiconductor device according to Preferred Embodiment 4 of the present invention.

As illustrated in FIG. 21B, an insulating coating material 46 is film-formed on the substrate 11 on which the plurality of electrodes 12 are provided. For example, the insulating coating material 46 is applied onto the substrate 11 and cured. As illustrated in FIG. 21C, the insulating coating material 46 on the first electrode 12a and the second electrode 12b is removed by, for example, photolithography while the insulating coating material 46 extending across the first electrode 12a and the second electrode 12b on the substrate 11 remains. As a result, the insulator 13 including the coupling insulating portion 13b disposed across the first electrode 12a and the second electrode 12b is formed. Further, the portions removed by the photolithography form the first opening 16a exposing a portion of the first electrode 12a on the substrate 11 and the second opening 16b exposing a portion of the second electrode 12b on the substrate 11.

On the substrate 11, the first exposed portion 17a and the second exposed portion 17b are preferably formed at positions where the first opening 16a and the second opening 16b are provided. The first exposed portion 17a is a portion exposed from the first opening 16a on the substrate 11. The second exposed portion 17b is a portion exposed from the second opening 16b on the substrate 11.

In a step ST13, as illustrated in FIG. 21D, the semiconductor sheet 14a is formed on the insulator 13 and the plurality of exposed portions 17. In detail, the step ST13 includes a step ST13A of forming the semiconductor sheet 14a continuous on the coupling insulating portion 13b, the first exposed portion 17a, and the second exposed portion 17b. In the step ST13A, the semiconductor sheet 14a is on an upper surface of the insulator 13 including the coupling insulating portion 13b. The semiconductor sheet 14a is deformed by its own weight at the first opening 16a and the second opening 16b, and is on the first exposed portion 17a and the second exposed portion 17b. The semiconductor sheet 14a is on the first electrode 12a positioned at the first exposed portion 17a. The semiconductor sheet 14a is on the second electrode 12b positioned at the second exposed portion 17b. For example, the step ST13 is preferably performed by a semiconductor sheet forming apparatus included in the manufacturing apparatus.

The semiconductor sheet 14a is continuously provided from the first electrode 12a positioned at the first exposed portion 17a to the second electrode 12b positioned at the second exposed portion 17b with the coupling insulating portion 13b interposed therebetween. Thus, the semiconductor sheet 14a electrically connects the first electrode 12a and the second electrode 12b.

In this way, the semiconductor device 1C is manufactured by performing the steps ST11 to ST13.

According to the semiconductor device 1C and the method of manufacturing the semiconductor device 1C according to Preferred Embodiment 4, the following advantageous effects can be obtained.

In the semiconductor device 1C, the insulator 13 includes the coupling insulating portion 13b disposed across the first electrode 12a and the second electrode 12b. The plurality of openings 16 include the first opening 16a exposing a portion of the first electrode 12a on the substrate 11 and the second opening 16b exposing a portion of the second electrode 12b on the substrate 11. The plurality of exposed portions 17 include the first exposed portion 17a exposed from the first opening 16a and the second exposed portion 17b exposed from the second opening 16b on the substrate 11. The semiconductor sheet 14a is continuously provided on the coupling insulating portion 13b, the first exposed portion 17a, and the second exposed portion 17b.

With this configuration, the performance of the device can be further improved. The semiconductor sheet 14a is continuously provided on the coupling insulating portion 13b, the first exposed portion 17a, and the second exposed portion 17b to improve adhesion. This makes it difficult for the semiconductor sheet 14a to be peeled off, thus improving durability.

In the semiconductor device 1C according to Preferred Embodiment 3, it is possible to freely select a base layer of the semiconductor sheet 14a as compared with Preferred Embodiment 1. It is known that the substrate 11 represented by $SiO_2$ defines and functions as a scattering source of carriers of graphene and significantly deteriorates electrical characteristics. In the semiconductor device 1C, an organic resin layer or a two dimensional insulating layer that is less likely to become an interference material with respect to the graphene can be selected as the base layer, and thus, the electrical characteristics of the graphene can be sufficiently provided.

At the plurality of exposed portions 17, the gap 18 is provided between the side wall 13a of the insulator 13 provided with the plurality of openings 16, the semiconductor sheet 14a, and the substrate 11. To be specific, at the first exposed portion 17a, a gap 18 is formed between a side wall 13a of the insulator 13 in which the first opening 16a is provided, the semiconductor sheet 14a, and the substrate 11. A gap 18 is formed between a side wall 13a of the insulator 13 provided with the second opening 16b, the semiconductor sheet 14a, and the substrate 11. With this configuration, stress applied to the semiconductor sheet 14a can be relaxed.

In Preferred Embodiment 4, the example in which the first opening 16a exposes a portion of the substrate 11 and a portion of the first electrode 12a, and the second opening 16b exposes a portion of the substrate 11 and a portion of the second electrode 12b has been described, but the present invention is not limited thereto. The first opening 16a only needs to expose the first electrode 12a. The second opening 16b only needs to expose the second electrode 12b. The first opening 16a and the second opening 16b do not need to expose the substrate 11.

Figure 22:
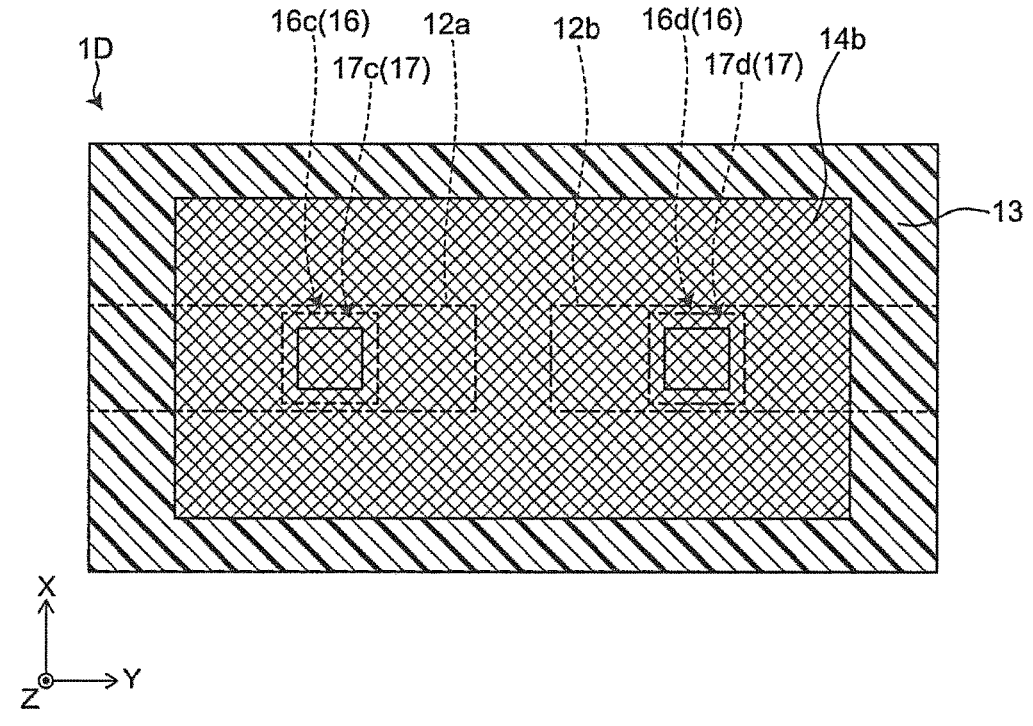
FIG. 22 is a schematic plan view illustrating an example of a main configuration of a semiconductor device according to a modification of Preferred Embodiment 4 of the present invention.

FIG. 22 is a schematic plan view illustrating an example of a main configuration of a semiconductor device 1D according to a modification of Preferred Embodiment 4 of the present invention. As illustrated in FIG. 22, in the semiconductor device 1D, a first opening 16c and a second opening 16d are provided in the insulator 13.

The first opening 16c exposes the first electrode 12a but do not expose the substrate 11. The second opening 16d exposes the second electrode 12b but do not expose the substrate 11. To be specific, when the semiconductor device 1D is viewed from the height direction (Z direction), the first opening 16c is preferably formed to be projectable on the upper surface of the first electrode 12a. When the semiconductor device 1D is viewed from the height direction (Z direction), the first opening 16c is formed within a range not protruding from the upper surface of the first electrode 12a. That is, dimensions of the first opening 16c in an X direction and a Y direction are smaller than dimensions of the upper surface of the first electrode 12a in the X direction and the Y direction. When the semiconductor device 1D is viewed from the height direction (Z direction), the second opening 16d is formed to be projectable on the upper surface of the second electrode 12b. When the semiconductor device 1D is viewed from the height direction (Z direction), the second opening 16d is formed within a range not protruding from the upper surface of the second electrode 12b. That is, dimensions of the second opening 16d in the X direction and the Y direction are smaller than dimensions of the upper surface of the second electrode 12b in the X direction and the Y direction.

In the semiconductor device 1D, a portion of the first electrode 12a is positioned at the first exposed portion 17c exposed from the first opening 16c. A portion of the second electrode 12b is positioned at the second exposed portion 17d exposed from the second opening 16d. The substrate 11 is not positioned at the first exposed portion 17c and the second exposed portion 17d.

The semiconductor sheet 14b is continuously provided on the coupling insulating portion 13b, the first exposed portion 17c, and the second exposed portion 17d. At the first exposed portion 17c, the semiconductor sheet 14b is on the first electrode 12a. At the second exposed portion 17d, the semiconductor sheet 14b is on the second electrode 12b. Thus, the first electrode 12a and the second electrode 12b can be electrically connected to each other by the semiconductor sheet 14b without disposing the semiconductor sheet 14b on the substrate 11.

With such a configuration, it is possible to reduce or prevent deterioration in electrical characteristics of the semiconductor sheet 14b due to the substrate 11. Further, the substrate 11 can be formed of a material freely selected. In the semiconductor device 1D, the substrate 11 can preferably be formed of, for example, a resin material such as PMMA, polyimide, styrene, PET, silicone or the like, or a two dimensional insulator material such as boron nitride.

Preferred Embodiment 5

A semiconductor device and a method of manufacturing a semiconductor device according to Preferred Embodiment 5 of the present invention will be described.

In Preferred Embodiment 5, differences from Preferred Embodiment 1 will be primarily described. In Preferred Embodiment 5, configurations identical or equivalent to those in Preferred Embodiment 1 will be denoted by the same reference signs and described. Additionally, in Preferred Embodiment 5, the description overlapping with Preferred Embodiment 1 will be omitted.

Preferred Embodiment 5 is different from Preferred Embodiment 1 in that the semiconductor sheet is preferably divided into a first semiconductor sheet on the insulator and a second semiconductor sheet on the exposed portion.

Figure 23:
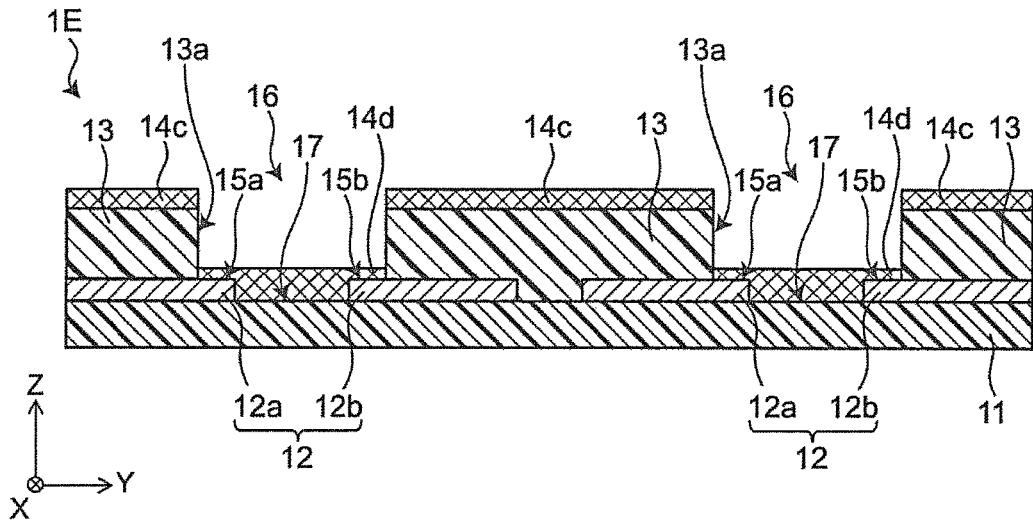
FIG. 23 is a schematic view illustrating an example of a main configuration of a semiconductor device according to Preferred Embodiment 5 of the present invention.
Figure 24:
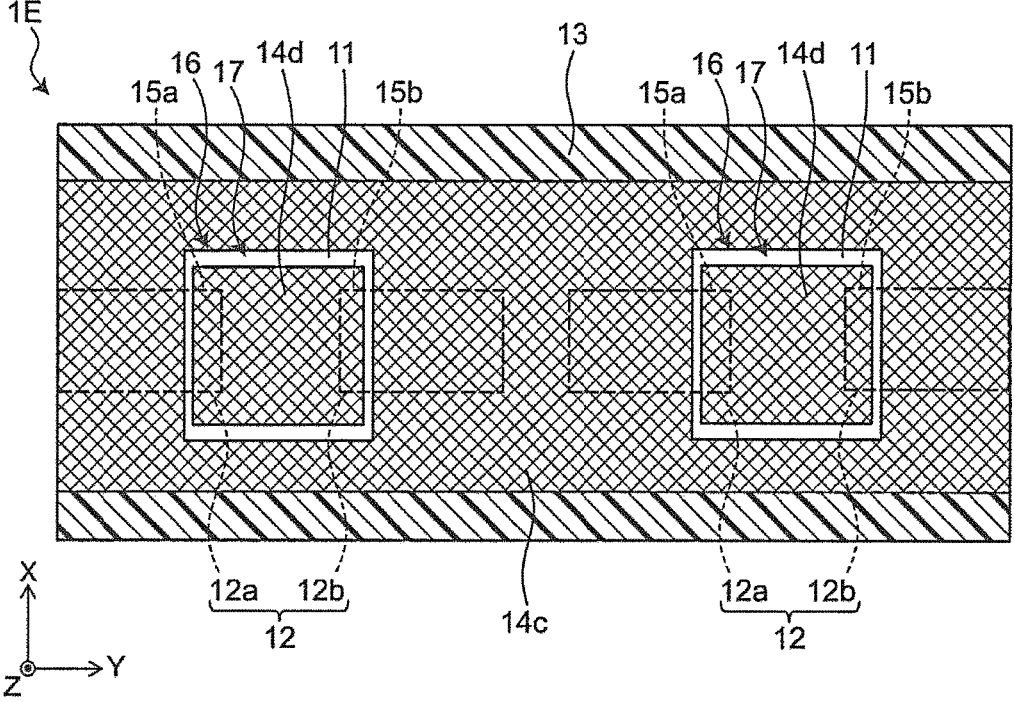
FIG. 24 is a schematic plan view illustrating an example of a main configuration of the semiconductor device according to Preferred Embodiment 5 of the present invention.

A semiconductor device 1E according to Preferred Embodiment 5 will be described with reference to FIG. 23 and FIG. 24. FIG. 23 is a schematic view illustrating an example of a main configuration of the semiconductor device 1E according to Preferred Embodiment 5 of the present invention. FIG. 24 is a schematic plan view illustrating an example of a main configuration of the semiconductor device 1E according to Preferred Embodiment 5 of the present invention.

As illustrated in FIG. 23 and FIG. 24, the semiconductor sheet 14 includes a first semiconductor sheet 14*c* and a second semiconductor sheet 14*d*. The first semiconductor sheet 14*c* is on the insulator 13. In particular, the first semiconductor sheet 14*c* is on the upper surface of the insulator 13. The second semiconductor sheet 14*d* is separated from the first semiconductor sheet 14*c* and on the exposed portion 17. The second semiconductor sheet 14*d* is on the first electrode 12*a* and the second electrode 12*b* that are positioned at the exposed portion 17, and electrically connects the first electrode 12*a* and the second electrode 12*b*. In Preferred Embodiment 5, the second semiconductor sheet 14*d* is in the region 15*a* including an end portion of the first electrode 12*a* opposing the second electrode 12*b* and the region 15*b* including an end portion of the second electrode 12*b* opposing the first electrode 12*a*.

Figure 25:
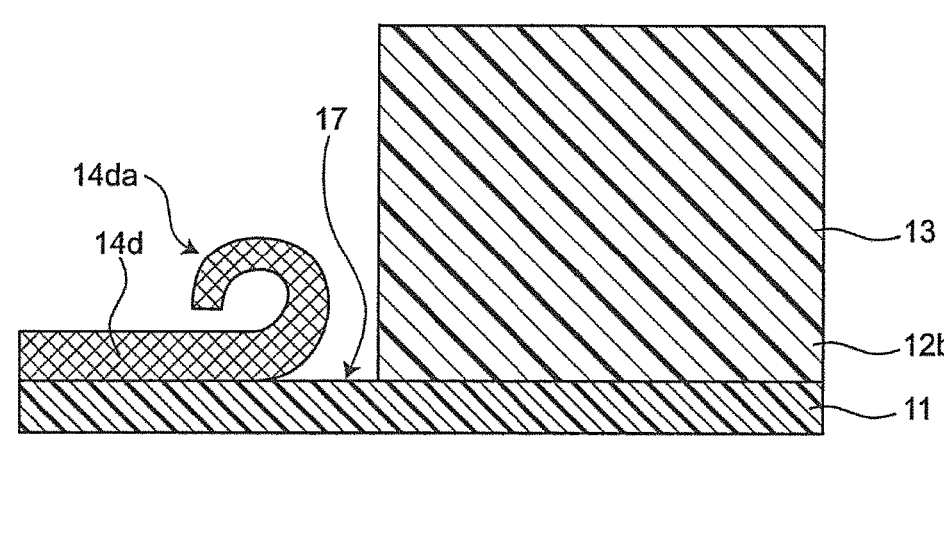
FIG. 25 is a schematic enlarged view in which a portion of an exposed portion is enlarged.

FIG. 25 is a schematic enlarged view in which a portion of the exposed portion 17 is enlarged. As illustrated in FIG. 25, an end portion 14*da* of the second semiconductor sheet 14*d* is bent in a thickness direction (Z direction) of the second semiconductor sheet 14*d*. The end portion 14*da* of the second semiconductor sheet 14*d* is bent in a direction away from the substrate 11. For example, when the semiconductor device 1E is viewed from a height direction (Z direction), the end portion 14*da* of the second semiconductor sheet 14*d* is bent to overlap the second semiconductor sheet 14*d*.

In the semiconductor device 1E, the end portion 14*da* of the second semiconductor sheet 14*d* can be easily checked when the semiconductor device 1E is viewed from the height direction (Z direction). This makes it possible to easily check that the second semiconductor sheet 14*d* is on the substrate 11.

Method of Manufacturing

Figure 26:
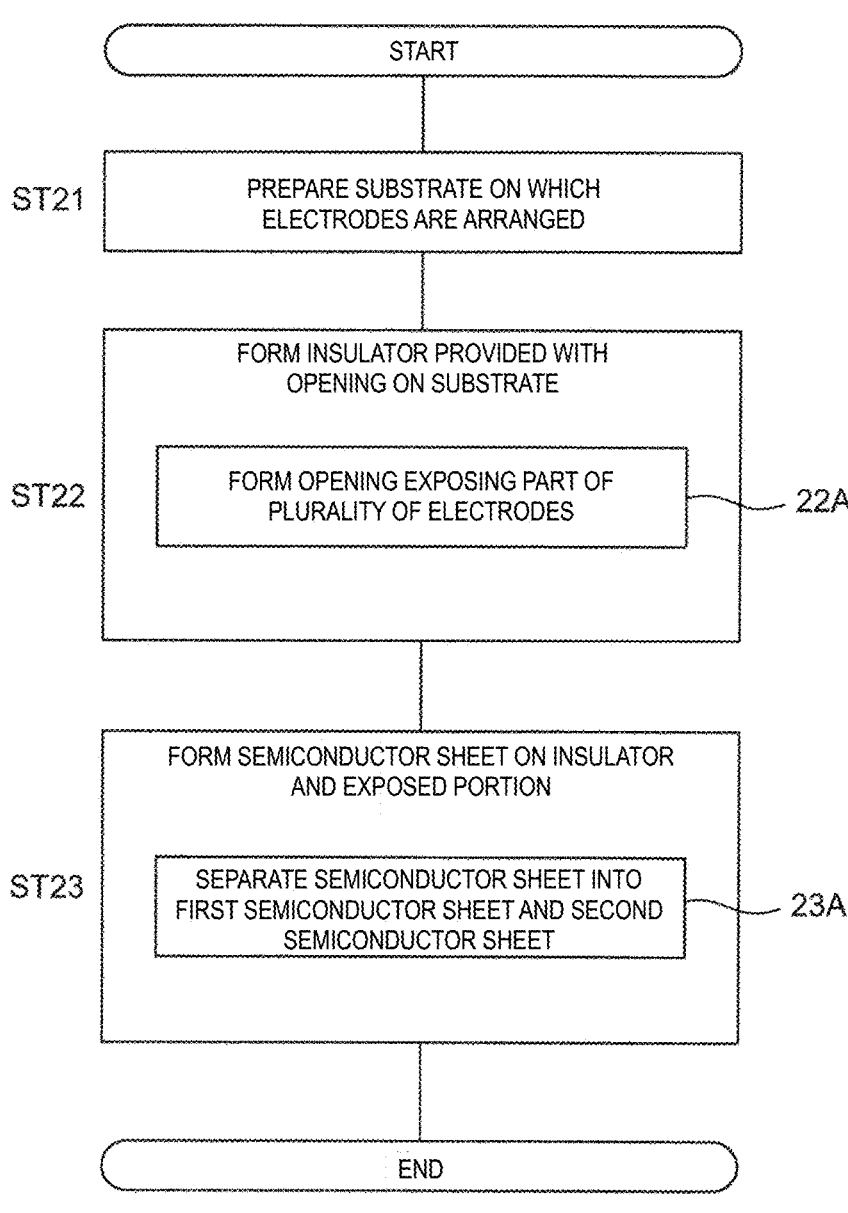
FIG. 26 is a flowchart of an example of a method of manufacturing a semiconductor device according to Preferred Embodiment 5 of the present invention.
Figure 27A:
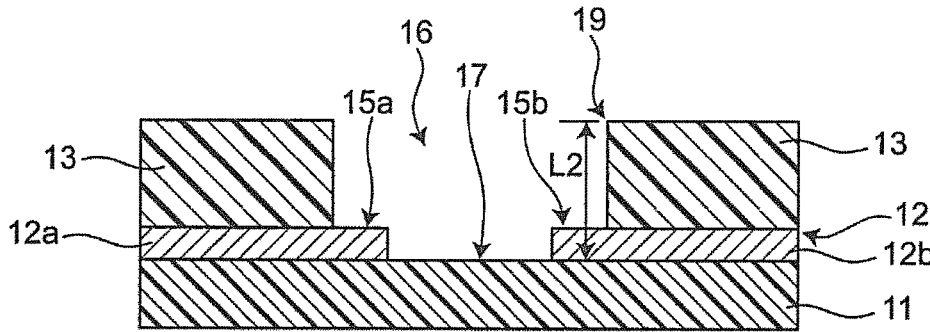
FIG. 27A is a schematic view illustrating an example of an operation in a process of forming a semiconductor sheet.
Figure 27B:
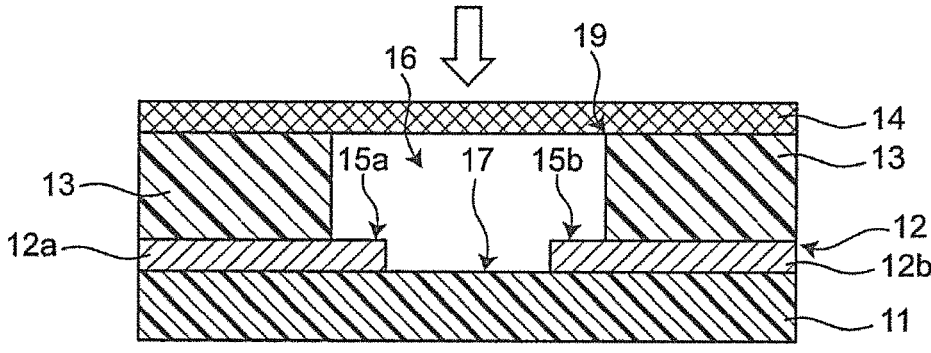
FIG. 27B is a schematic view illustrating an example of an operation in the process of forming the semiconductor sheet.
Figure 27C:
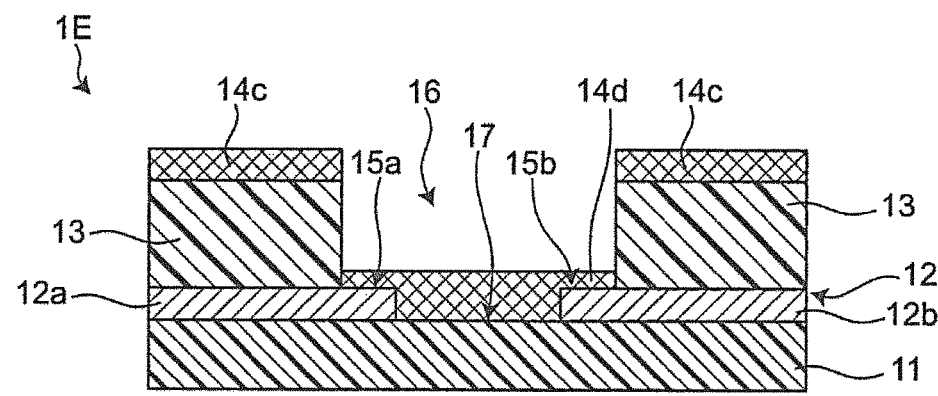
FIG. 27C is a schematic view illustrating an example of an operation in the process of forming the semiconductor sheet.

An example of a method of manufacturing the semiconductor device 1E will be described. FIG. 26 is a flowchart of an example of the method of manufacturing the semiconductor device 1E according to Preferred Embodiment 5 of the present invention. FIGS. 27A to 27C are schematic views illustrating an example of operations in a process of forming a semiconductor sheet by transfer. Steps that will be described below are executed by a manufacturing apparatus. Since steps ST21 and ST22 are the same as or similar to the steps ST1 and ST2 illustrated in FIG. 6 of Preferred Embodiment 1, detailed description thereof will be omitted.

As illustrated in FIG. 26, in the step ST21, the substrate 11 on which a plurality of electrodes 12 are provided is prepared. For example, the step ST21 is preferably performed by a metal film forming apparatus represented by a sputtering apparatus or an electron beam (EB) vapor deposition apparatus included in the manufacturing apparatus. In the step ST22, the insulator 13 including the coating portion 15 provided with the opening 16 is formed on the substrate 11. For example, the step ST22 is preferably performed by an insulating film forming apparatus represented by a spin coater, various vapor deposition apparatuses, and a CVD apparatus that are included in the manufacturing apparatus, and a photolithography apparatus.

The step ST22 includes a step ST22A of forming the opening 16 exposing a portion of the plurality of electrodes 12. In the step ST22A, the opening 16 is formed to expose a portion of the first electrode 12*a* and a portion of the second electrode 12*b*. The portion of the first electrode 12*a* and the portion of the second electrode 12*b* are positioned at the exposed portion 17 exposed by the opening 16 on the substrate 11. In Preferred Embodiment 5, the region 15*a* including an end portion of the first electrode 12*a* opposing the second electrode 12*b* and the region 15*b* including an end portion of the second electrode 12*b* opposing the first electrode 12*a* are positioned at the exposed portion 17.

In a step ST23, the semiconductor sheet 14 is formed on the insulator 13 and the exposed portion 17. To be specific, in the step ST23, the first semiconductor sheet 14*c* on the insulator 13 and the second semiconductor sheet 14*d* on the exposed portion 17 exposed from the opening 16 on the substrate 11 are formed. For example, the step ST23 is preferably performed by a semiconductor sheet forming apparatus included in the manufacturing apparatus.

The step ST23 includes a step ST23A of separating the semiconductor sheet 14 into the first semiconductor sheet 14*c* and the second semiconductor sheet 14*d*.

In the step ST23A, the semiconductor sheet 14 is divided into the first semiconductor sheet 14*c* on the insulator 13 and the second semiconductor sheet 14*d* on the exposed portion 17 exposed from the opening 16 on the substrate 11.

For example, as illustrated in FIGS. 27A to 27C, in the step ST23A, the semiconductor sheet 14 is cut by a step 19 formed by the insulator 13 and the substrate 11 at the opening 16. As a result, the semiconductor sheet 14 is separated into the first semiconductor sheet 14*c* and the second semiconductor sheet 14*d*.

As illustrated in FIG. 27A, the step 19 is formed by the insulator 13 and the substrate 11. A size of the step 19 is determined by a distance L2 from the substrate 11 to the upper surface of the insulator 13. By adjusting the size (distance L2) of the step 19, the semiconductor sheet 14 can be cut by utilizing the own weight of the semiconductor sheet 14. For example, the size (distance L2) of the step 19 is equal to or larger than 100 nm and equal to or smaller than 1 mm.

As illustrated in FIG. 27B, when the semiconductor sheet 14 is transferred from above the insulator 13, the semiconductor sheet 14 deforms due to its own weight at the opening 16. To be more specific, at the opening 16, the semiconductor sheet 14 deforms in a direction approaching a portion of the first electrode 12*a* and a portion of the second electrode 12*b* that are positioned at the exposed portion 17.

In order to bring the semiconductor sheet 14 into close contact with a side surface of the insulator 13, the region 15*a*, the region 15*b*, and the exposed portion 17, the semiconductor sheet 14 needs to be stretched by deformation. When the size (distance L2) of the step 19 is sufficiently small, and the semiconductor sheet 14 has small rigidity and sufficiently large ductility, the semiconductor sheet 14 is stretched without being broken and comes into close contact with the side surface of the insulator 13, the region 15*a*, the region 15*b*, and the exposed portion 17. When the size (distance L2) of the step 19 is large and the rigidity and ductility of the semiconductor sheet 14 are small, the semiconductor sheet 14 is deformed by its own weight, and as a result, the semiconductor sheet 14 cannot be sufficiently stretched and is cut. At this time, the end portion of the insulator 13 to which the most stress is applied is broken.

When the rigidity of the semiconductor sheet 14 is large, the semiconductor sheet 14 is not deformed and is not cut, and bridges the insulator 13 and the insulator 13 at the upper portion of the exposed portion 17. However, in this state, the first electrode 12*a* and the second electrode 12*b* are not electrically connected to the semiconductor sheet, so that the semiconductor sheet 14 does not operate as a semiconductor device.

As illustrated in FIG. 27C, by cutting the semiconductor sheet 14 due to the step 19, the first semiconductor sheet 14*c* is on the insulator 13, and the second semiconductor sheet 14*d* is on the exposed portion 17.

In this way, the semiconductor device 1E is manufactured by performing the steps ST21 to ST23.

According to the semiconductor device 1E and the method of manufacturing the semiconductor device 1E according to Preferred Embodiment 5, the following advantageous effects can be obtained.

In the semiconductor device 1E, the exposed portion 17 includes a portion of the first electrode 12*a* and a portion of the second electrode 12*b*. The semiconductor sheet 14 includes the first semiconductor sheet 14*c* on the insulator 13 and the second semiconductor sheet 14*d* separated from the first semiconductor sheet 14*c* and on the exposed portion 17.

With such a configuration, an electrical short circuit of the semiconductor sheet 14 can be interrupted. In addition, since the first semiconductor sheet 14*c* and the second semiconductor sheet 14*d* are physically separated from each other, even when a physical load is applied to the first semiconductor sheet 14*c*, the second semiconductor sheet 14*d* is not affected. For this reason, when a physical load is applied from the outside, it is possible to reduce or prevent deterioration in performance of the semiconductor device 1E due to peeling of the semiconductor sheet 14.

The end portion 14*da* of the second semiconductor sheet 14*d* is bent in the thickness direction (Z direction) of the second semiconductor sheet 14*d*. With such a configuration, the region where the second semiconductor sheet 14*d* is arranged can be easily checked. In addition, it is possible to reduce or prevent adsorption of the target molecule 50 to the end portion 14*da* of the second semiconductor sheet 14*d*.

In the method of manufacturing the semiconductor device 1E, the step ST22 of forming the insulator 13 includes the step ST22A of forming the opening 16 in the insulator 13 to expose a portion of the first electrode 12*a* and a portion of the second electrode 12*b* on the substrate 11. The step ST23 of forming the semiconductor sheet 14 includes the step ST23A of separating the semiconductor sheet 14 into the first semiconductor sheet 14*c* on the insulator 13 and the second semiconductor sheet 14*d* on the exposed portion 17 exposed from the opening 16 on the substrate 11.

In the step ST23A of separating, the semiconductor sheet 14 is cut at the opening 16 by the step 19 formed by the insulator and the substrate 11. With such a configuration, the semiconductor sheet 14 can be easily separated into the first semiconductor sheet 14*c* and the second semiconductor sheet 14*d*.

In addition, in the method of manufacturing according to Preferred Embodiment 5, the etching process of the semiconductor sheet 14 in the forming step of the method of manufacturing according to Preferred Embodiment 1 can be omitted.

In Preferred Embodiment 5, the example in which the semiconductor sheet 14 is formed by transfer in the step ST23 has been described, but the present invention is not limited thereto. For example, in the step ST23, the semiconductor sheet 14 may be formed by sticking, growing, or coating.

Although the present invention has been sufficiently described in connection with the preferred embodiments with reference to the accompanying drawings, various changes and modifications will be apparent to those skilled in the art. Such variations and modifications are to be understood as included within the scope of the present invention as defined by the appended claims unless they depart therefrom.

The semiconductor devices according to preferred embodiments of the present invention are useful for a chemical sensor to detect ions or a biosensor to detect viruses or the like.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A semiconductor device comprising;
a substrate;
a plurality of electrodes on the substrate;
an insulator provided over the plurality of electrodes and with one opening or a plurality of openings exposing at least one electrode among the plurality of electrodes on the substrate, the insulator covering at least a portion of the plurality of electrodes; and
a semiconductor sheet over the insulator and covering one or a plurality of exposed portions exposed from the one opening or the plurality of openings on the substrate; wherein
when viewed from the height direction of the substrate, the plurality of electrodes are exposed from the insulator also at portions other than the one opening or the plurality of openings, and an area of the insulator is larger than an area of the plurality of electrodes exposed from the insulator.

2. The semiconductor device according to claim 1, wherein
the plurality of electrodes include a first electrode, and a second electrode at an interval from the first electrode;
at least one of a portion of the first electrode and a portion of the second electrode is positioned at the one or the plurality of exposed portions; and
the semiconductor sheet is connected to the first electrode and the second electrode.

3. The semiconductor device according to claim 2, wherein a region including an end portion of the first electrode opposing the second electrode and a region including an end portion of the second electrode opposing the first electrode are positioned at the one or the plurality of exposed portions.

4. The semiconductor device according to claim 2, wherein the insulator includes a coupling insulating portion positioned across the first electrode and the second electrode;
the plurality of openings include a first opening exposing a portion of the first electrode on the substrate and a second opening exposing a portion of the second electrode on the substrate;
the plurality of exposed portions include a first exposed portion exposed from the first opening on the substrate and a second exposed portion exposed from the second opening on the substrate; and
the semiconductor sheet is continuously provided on the coupling insulating portion, the first exposed portion, and the second exposed portion.

5. The semiconductor device according to claim 4, wherein
a gap is provided between a side wall of the insulator provided with the plurality of openings, the semiconductor sheet, and the substrate.

6. The semiconductor device according to claim 3, wherein
the semiconductor sheet includes:

a first semiconductor sheet on the insulator; and a second semiconductor sheet separated from the first semiconductor sheet and on the exposed portion.

7. The semiconductor device according to claim 6, wherein an end portion of the second semiconductor sheet is bent in a thickness direction of the second semiconductor sheet.

8. The semiconductor device according to claim 1, wherein the semiconductor sheet is made of at least one of graphene, a carbon nanotube, an organic semiconductor, MXENES, and a transition metal dichalcogenide layered material.

9. The semiconductor device according to claim 1, further comprising:

a plurality of receptors on the semiconductor sheet and structured to capture a target molecule.

10. The semiconductor device according to claim 9, further comprising:

a calculator configured to receive an electric signal output from the semiconductor sheet and configured to calculate an amount of the target molecule based on the electric signal.

11. The semiconductor device according to claim 1, wherein the semiconductor sheet is in close contact with the insulator and the one or the plurality of exposed portions by van der Waals force.

12. The semiconductor device according to claim 2, further comprising:

a calculator configured to receive an electric signal output from the semiconductor sheet and configured to calculate an amount of the target molecule based on the electric signal; wherein the calculator is connected to the first electrode, the second electrode, and a third electrode; and the third electrode is arranged above the semiconductor sheet.

13. The semiconductor device according to claim 12, wherein the calculator controls a first voltage applied between the first electrode and the second electrode and a second voltage applied to the third electrode.

14. The semiconductor device according to claim 10, wherein the electric signal output from the semiconductor sheet changes according to a surface charge of the target molecules.

15. A method of manufacturing a semiconductor device comprising:

preparing a substrate on which a plurality of electrodes are provided;

forming an insulator over the plurality of electrodes and provided with one or a plurality of openings exposing at least one electrode among the plurality of electrodes on the substrate, the insulator covering the plurality of electrodes; and forming a semiconductor sheet over the insulator and to cover one or a plurality of exposed portions exposed from the one or the plurality of openings on the substrate; wherein when viewed from the height direction of the substrate, the plurality of electrodes are exposed from the insulator also at portions other than the one or the plurality of openings, and an area of the insulator is larger than an area of the plurality of electrodes exposed from the insulator.

16. The method of manufacturing the semiconductor device according to claim 15, wherein the plurality of electrodes include a first electrode and a second electrode at an interval from the first electrode;

at least one of a portion of the first electrode and a portion of the second electrode is positioned at the one or the plurality of exposed portions; and the semiconductor sheet electrically connects the first electrode and the second electrode to each other.

17. The method of manufacturing the semiconductor device according to claim 16, wherein a region including an end portion of the first electrode opposing the second electrode and a region including an end portion of the second electrode opposing the first electrode are positioned at the one exposed portion.

18. The method of manufacturing the semiconductor device according to claim 16, wherein the forming of the insulator includes:

forming a coupling insulating portion across the first electrode and the second electrode; and forming, in the insulator, a first opening exposing a portion of the first electrode on the substrate and a second opening exposing a portion of the second electrode on the substrate; and the forming of the semiconductor sheet includes continuously forming the semiconductor sheet on the coupling insulating portion, a first exposed portion exposing the portion of the first electrode from the first opening, and a second exposed portion exposing the portion of the second electrode from the second opening.

19. The method of manufacturing the semiconductor device according to claim 17, wherein the forming of the insulator includes forming, in the insulator, an opening exposing a portion of the first electrode and a portion of the second electrode on the substrate; and the forming of the semiconductor sheet includes separating the semiconductor sheet into a first semiconductor sheet on the insulator and a second semiconductor sheet on an exposed portion exposed from the opening on the substrate.

20. The method of manufacturing the semiconductor device according to claim 19, wherein the separating includes cutting the semiconductor sheet by a step formed by the insulator and the substrate at the opening.

* * * * *